(12) United States Patent
Goral et al.

(10) Patent No.: US 6,779,998 B2
(45) Date of Patent: Aug. 24, 2004

(54) GAS ASSIST MOLDING OF ONE-PIECE CATHETERS

(75) Inventors: David Goral, Brookfield, CT (US); Adel Kafrawy, Kingston, MA (US); William F. Polley, Duncanville, TX (US); Joseph R. Thomas, Southlake, TX (US)

(73) Assignee: Medex, Inc., Carlsbad, CA (US)

( * ) Notice: Subject to any disclaimer, the term of this patent is extended or adjusted under 35 U.S.C. 154(b) by 0 days.

(21) Appl. No.: 10/269,757

(22) Filed: Oct. 10, 2002

(65) Prior Publication Data

US 2003/0044484 A1 Mar. 6, 2003

Related U.S. Application Data

(62) Division of application No. 09/476,411, filed on Dec. 30, 1999, now Pat. No. 6,630,086.

(51) Int. Cl.[7] .................... B29C 45/14; B29C 45/16; B29C 45/26

(52) U.S. Cl. .................... 425/112; 425/120; 425/130

(58) Field of Search .................. 425/130, 120, 425/112, 536; 264/572

(56) References Cited

U.S. PATENT DOCUMENTS

| | | | | |
|---|---|---|---|---|
| 3,385,553 A | * | 5/1968 | Braun | 425/577 |
| 3,983,203 A | * | 9/1976 | Corbett | 264/150 |
| 4,750,877 A | * | 6/1988 | McFarlane | 425/577 |
| 5,510,065 A | * | 4/1996 | McFarlane | 264/328.12 |
| 5,620,639 A | * | 4/1997 | Stevens et al. | 264/572 |
| 5,972,256 A | * | 10/1999 | Wurst et al. | 264/40.1 |
| 6,192,568 B1 | * | 2/2001 | Kafrawy et al. | 264/157 |
| 6,623,688 B2 | * | 9/2003 | Gedritis et al. | 264/572 |

* cited by examiner

Primary Examiner—Robert B. Davis
(74) Attorney, Agent, or Firm—Wood, Herron & Evans, LLP

(57) ABSTRACT

An apparatus is disclosed for manufacturing an integral one-piece catheter having a tube and a hub. A mold having a mold cavity into which molten polymer is fed to form the hub and tube, and into which gas is injected into an inlet of the mold.

26 Claims, 38 Drawing Sheets

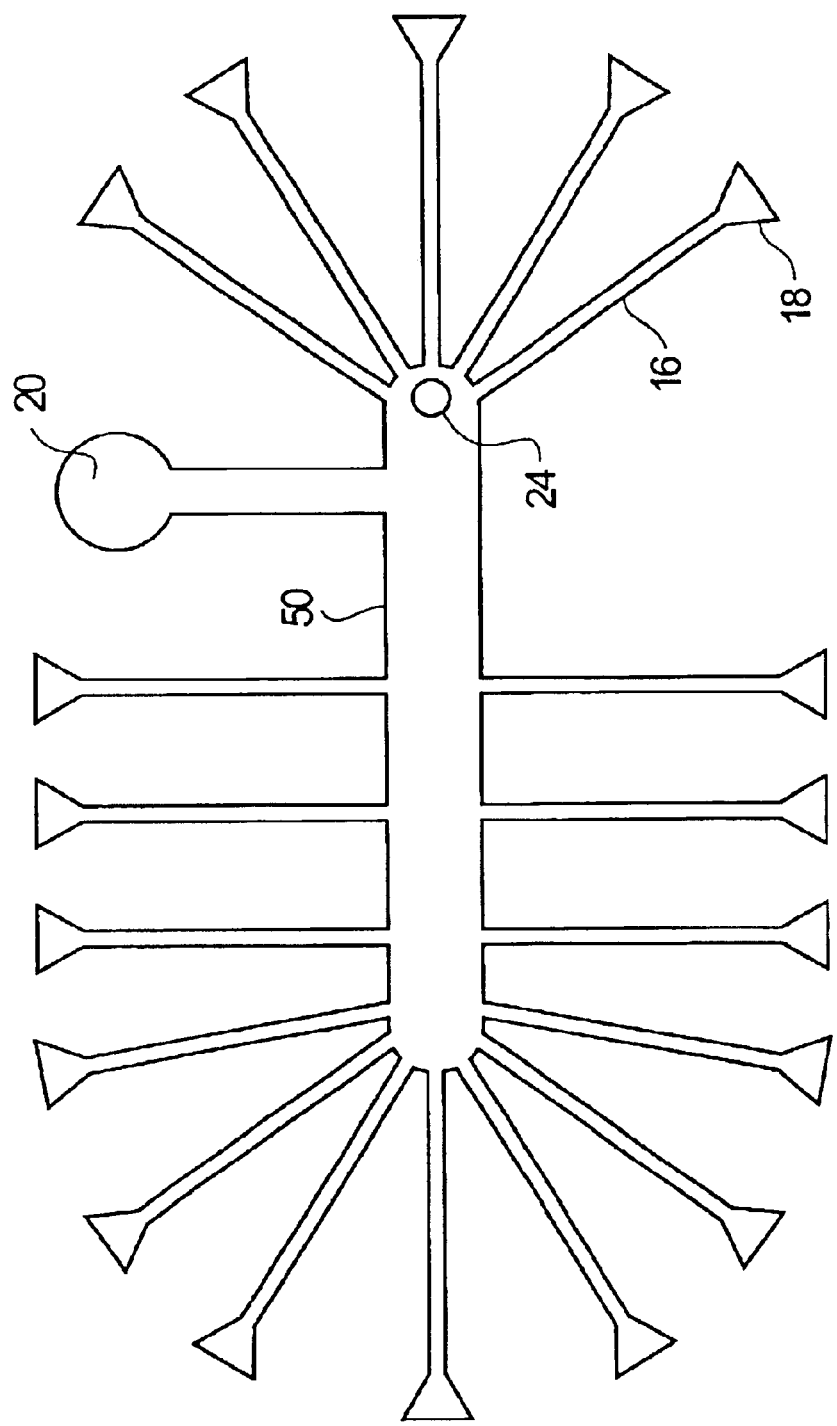

GAS ASSIST MOLDING OF ONE-PIECE CATHETERS

CROSS REFERENCE TO RELATED APPLICATION

This is a divisional of Ser. No. 09/476,411, filed on Dec. 30, 1999 and now U.S. Pat. No. 6,630,086, entitled GAS ASSISTED MOLDING OF ONE-PIECE CATHETERS.

BACKGROUND OF THE INVENTION

1. Field of the Invention

This invention relates generally to a method of forming an intravascular device and more specifically for fabricating a catheter device.

2. Description of Related Art

Intravascular devices such as catheter assemblies are generally used for passing fluids between a device such as a syringe or a drip to or from body lumens such as veins or arteries, or other internal target sites. Such an assembly usually includes a hub, a catheter tube, and a needle. An eyelet ring is typically inserted into the catheter tube. The catheter tube, together with the eyelet ring, is then inserted into an opening in the nose of the hub and is secured to the hub by press fitting the eyelet ring within the nose of the hub. This hub and tube assembly is then mounted over a sharp needle which is in turn attached to a plastic hub. The sharp tip of the needle is used for piercing a body lumen so that access may be gained into the body lumen by the needle and subsequently the catheter. Once the catheter and the needle are located within the body lumen, the needle is removed and discarded while the catheter tube remains in the body lumen. A syringe or a tube of a drip is then attached to the hub so that fluids may be passed through the hub and the catheter between the drip or the syringe and the body lumen. The hub is typically made of materials that provide sufficient rigidity to securely attach drip lines thereto and the catheter tube is usually made of a material which is flexible and soft to minimize bodily injury.

Hubs used in catheter assemblies are generally made by using injection molding. However, over-the-needle catheter tubes are usually made by an extrusion process and cut into short pieces instead of a single injection molded piece for two reasons. First, it is generally considered impractical to use a core pin of the same length as the tube in a conventional core pin injection molding process. This is because the core pin is often bent or broken in a high speed manufacturing environment resulting in frequent down time. Second, it is also generally thought by those skilled in the art that the gas assisted injection molding process cannot be used because the length of the tube in relation to the thickness of the thin wall exceeds the generally accepted aspect ratio of greater than 200. The aspect ratio is the length of the cylinder or tube divided by the wall thickness of that cylinder or tube.

Although plastic needles have been manufactured using injection molding with gas assist manufacturing as shown in U.S. Pat. No. 5,620,639 issued to Stevens et al., a plastic needle is very different than a catheter. First, the geometry of a needle is quite different from that of an intravenous catheter. A needle requires the presence of a sharp point on the distal end of the needle to ease the penetration of the needle into the vascular system, whereas an over-the-needle catheter requires a bevel or taper at the distal end in order to provide a smooth entry of the catheter into the vascular system. The bevel must fit precisely over the needle to allow for the smooth entry of the catheter into the vascular system with the least trauma to the patient. Second, a needle requires the use of a high modulus material for the efficient penetration of the vascular system in contrast to catheters that require flexible and soft materials to minimize bodily injury. Materials with tensile modulii above 10,000 megapascals (MPa), such as liquid crystal polymers and fiber-filled polyamides, are generally suitable for the production of plastic needles whereas materials with tensile modulii of less than 300 MPa are suitable for catheters. Additionally, over-the-needle catheters must have flow rates of the fluids that are to be provided to the patient to conform with ISO International Standard 10555-5, whereas there is no such standard for needles. It is therefore desirable to use a material capable of forming a lengthy, soft and flexible tube for an intravascular device that includes a bevel at the distal end of the tube and a luer lock at the proximal end of a hub.

SUMMARY OF THE INVENTION

An apparatus and a method are disclosed for manufacturing an integral one-piece catheter having a tube and a hub by using a gas assisted injection molding process. The method comprises feeding molten material into a mold having a mold cavity. In one embodiment, the molten material is injected near or into the hub portion of the cavity. In another embodiment, the molten material is injected into the catheter tube portion of the mold. While the polymer is introduced into the cavity, a fluid such as a gas is then injected through an inlet of the mold into the material in the cavity forming a channel throughout the center of the injected material. This may also cause a portion of the molten polymer to be displaced by the gas into a spillover exit.

Another embodiment of the invention involves forming a first portion of an intravascular device using a first material in a first mold. Thereafter the first portion of the intravascular device is inserted into a second mold to form a second portion using a second material. The second mold is formed on or around the first mold. A fluid such as a gas is then injected through an inlet of the mold into the cavity forming a channel throughout the center of the tube cavity. This may result in a portion of the molten polymer to be displaced by the gas into a spillover exit area.

In yet another embodiment of the invention, a first portion of the mold is injected with a first material, and a second portion of the cavity is injected with a second material at or around the same time that the first material is injected into the first portion of the cavity. A fluid such as a gas is injected through an inlet of the mold into the cavity. This causes a portion of the molten polymer to be displaced by the gas to conform to the mold with excess material displaced into the spillover exit area. In another embodiment of the invention, injected polymer is precisely measured to prevent spillover of excess molten polymer. In both of the previous cases, a hollow channel is formed throughout the center of the tube cavity.

Additional features, embodiments, and benefits will be evident in view of the figures and detailed description presented herein.

BRIEF DESCRIPTION OF THE DRAWINGS

The features, aspects, and advantages of the invention will become more thoroughly apparent from the following detailed description, appended claims, and accompanying drawings in which:

FIG. 38 shows a mold with multiple cavities for forming intravascular devices.

DETAILED DESCRIPTION OF THE INVENTION

Figure 1:
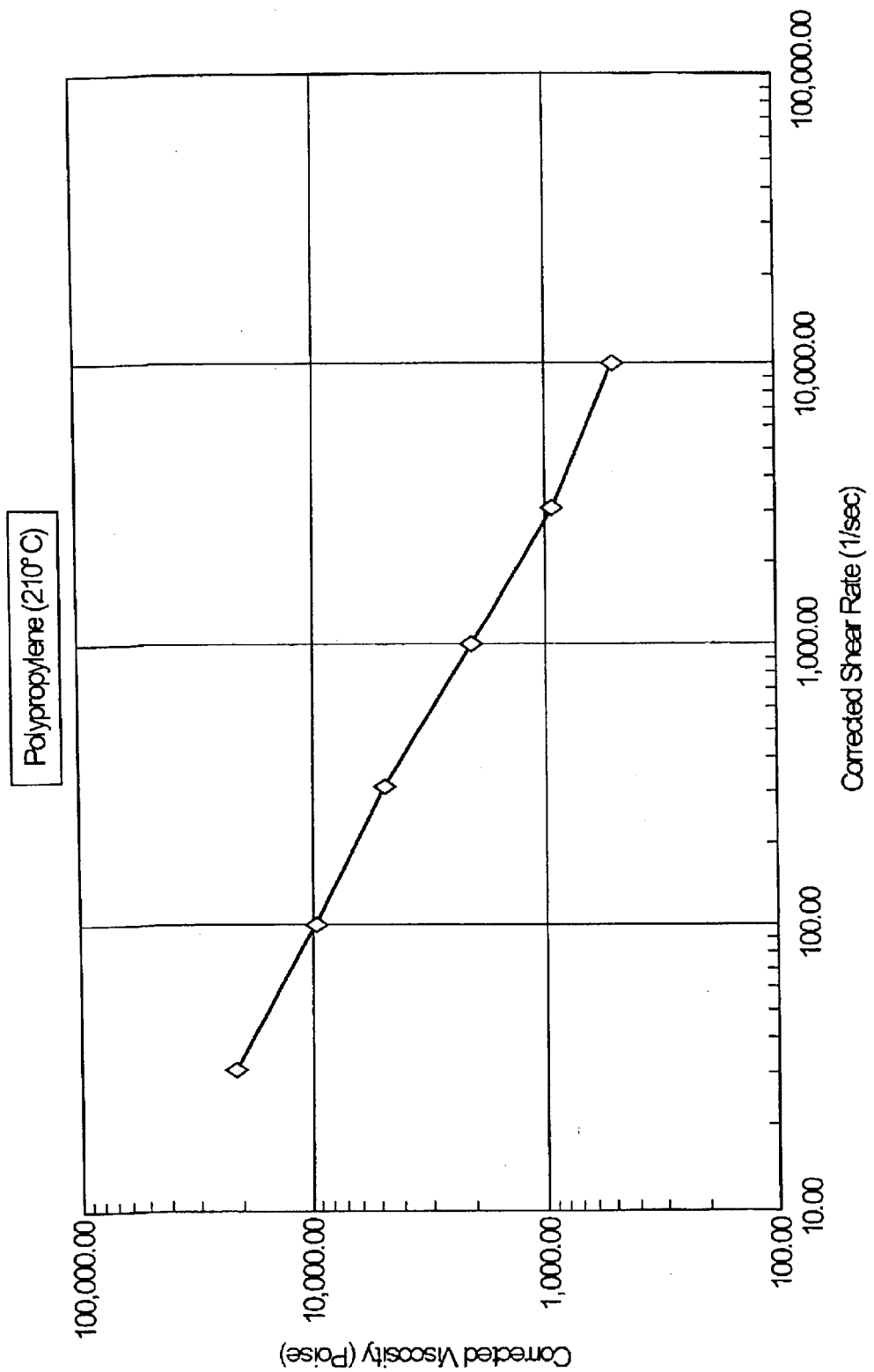
FIG. 1 shows the rheological properties (i.e., viscosity versus shear rate) of polypropylene.

In the description that follows, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

One embodiment of the invention relates to forming a one-piece catheter using gas assist injection molding manufacturing of material described below. The catheter may be formed by using two separate cavities that form a first portion and a second portion. Additionally, a first polymer and a second polymer may be injected into each cavity. In another embodiment, a one-piece catheter may be formed from a single cavity using one polymer. In another embodiment of the invention, a connector such as a luer lock may be formed. The luer lock allows for the fastening of external delivery tubing to the hub of the intravenous device.

There are significant advantages to using gas assist injection molding manufacturing in order to form a one-piece catheter tube and hub compared to the conventional method of injection molding of the hub, extrusion of the tube, and assembling of both of these elements using an eyelet. The gas assist injection molding manufacture of a one-piece catheter typically costs less than that of the traditional method used to manufacture a catheter (i.e., (a) injection molding of the hub, (b) extrusion of the catheter tube, and (c) the assembly of both using an eyelet). Moreover, the time used for forming a one-piece catheter is reduced due to the ease of using a single gas assist injection process. The one-piece catheter gas assist injection molding process is also less complicated than the conventional processes listed in (a) through (c) provided above. For example, assembly of two or more pieces is not required of the device formed from practicing the invention. Additionally, the bevel at the distal end of the tube does not have to be formed using subsequent thermal or laser operations because the mold incorporates the bevel shape directly into the mold itself.

Quality and productivity is also increased using the one-piece gas assist manufacturing process. For example, when a hub and a tube are separately formed, the hub may have a defect at the nose section of the hub that may not be noticed until after a hub is fitted to a tube. A large amount of hubs may have been formed before the defect is discovered thereby decreasing productivity. Similarly, in traditional manufacturing, tubing produced with dimensional errors results in numerous tubes that must be discarded. In comparison, a one-piece catheter eliminates this problem by forming the entire one-piece catheter simultaneously or at about the same time using a mold that incorporates the precise dimensions required by a particular catheter device.

In the discussion provided below, the materials and equipment used to practice the invention are provided followed by the dimensions of the portions (e.g., hub and tube) of the one-piece catheter that may be fabricated practicing the invention. Thereafter, numerous embodiments of the invention are presented.

Selection of Material for Hub

Figure 2:
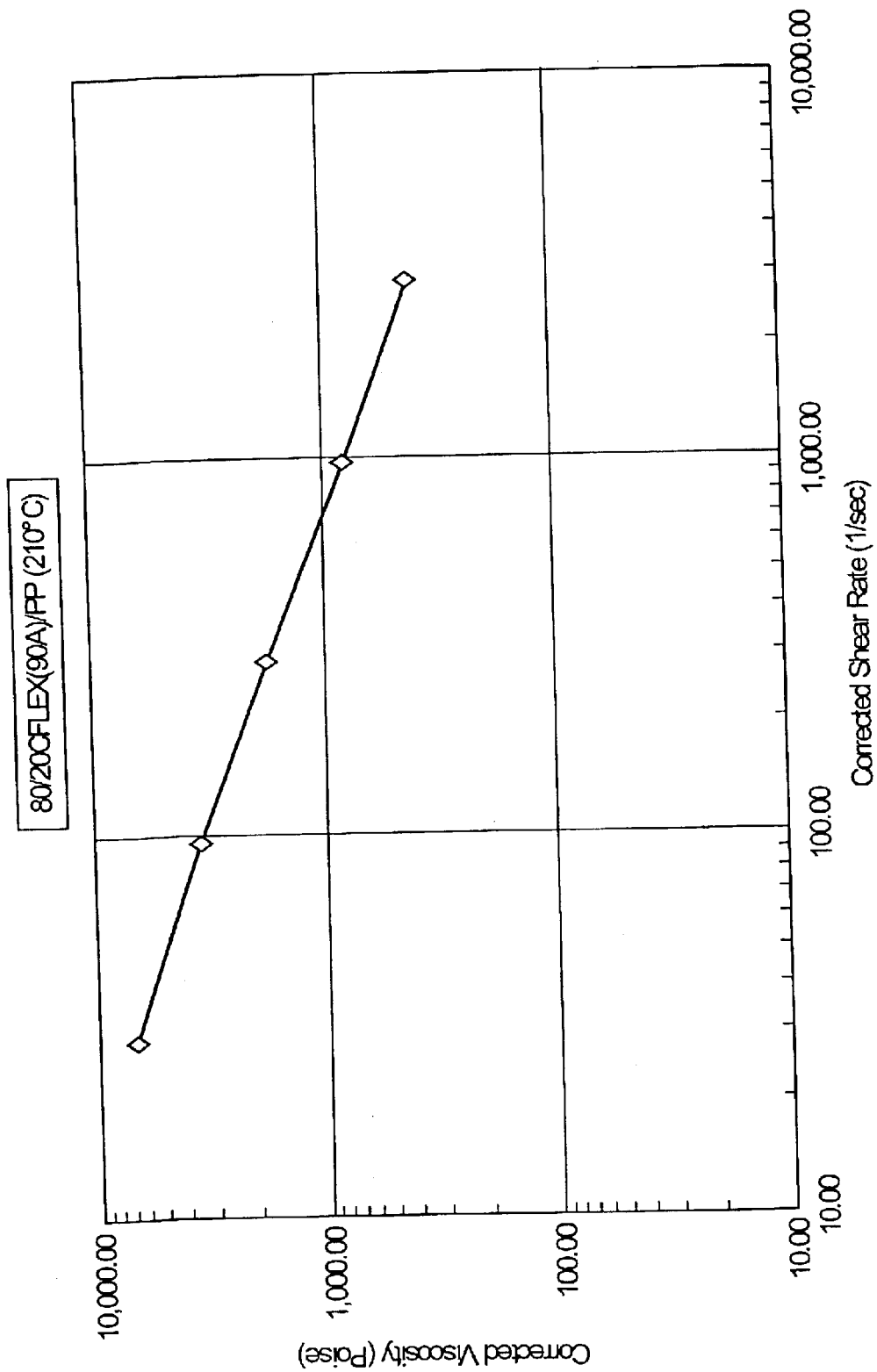
FIG. 2 shows the rheological properties (i.e., viscosity versus shear rate) of a thermoplastic elastomer sold under the trademark of C-FLEX™ blended with polypropylene at a weight percent ratio of 80/20.
Figure 3:
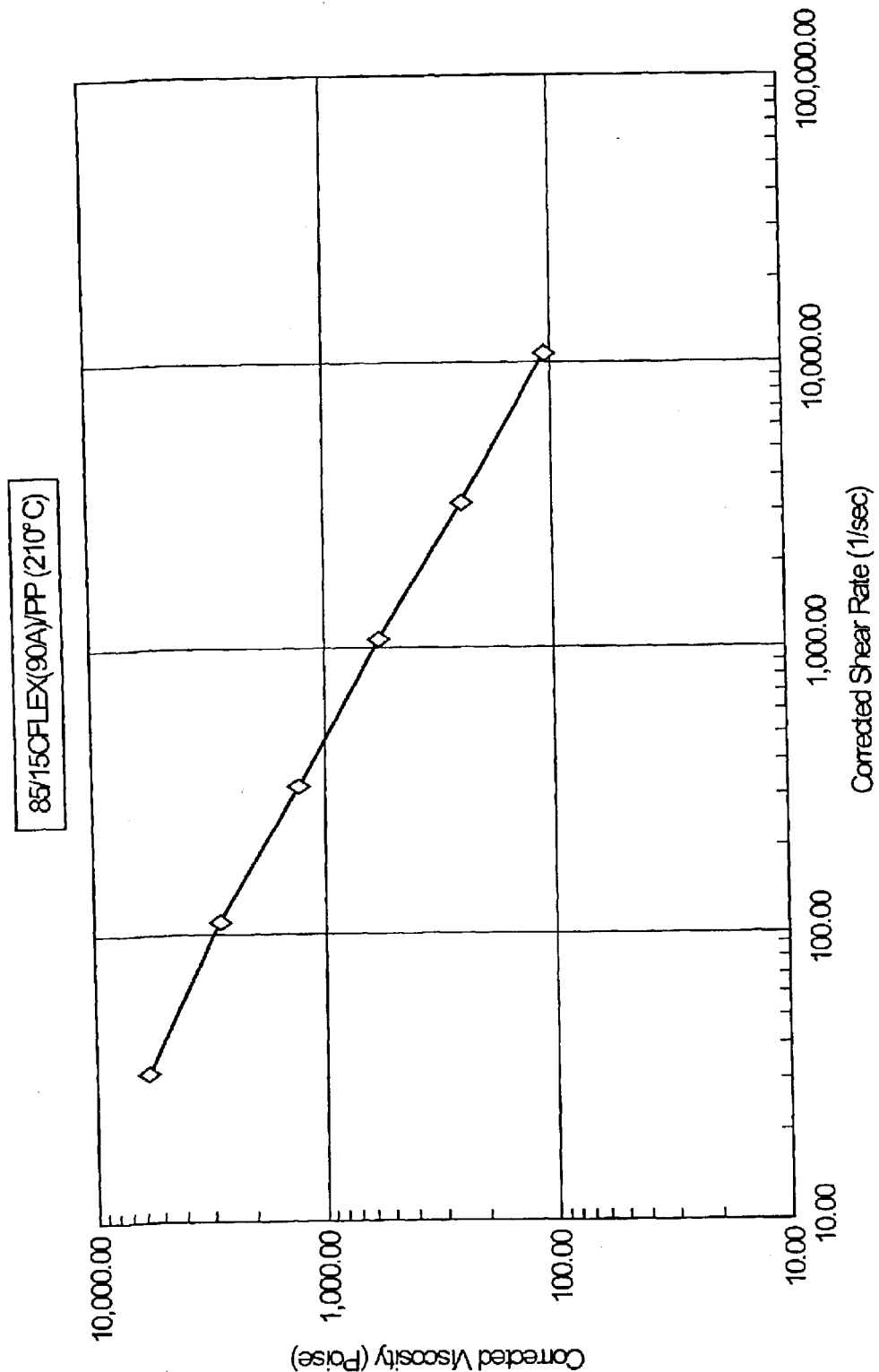
FIG. 3 shows the Theological properties (i.e., viscosity versus shear rate) of a thermoplastic elastomer sold under the trademark of C-FLEX™ blended with polypropylene at a weight percent ratio of 85/15.
Figure 4:
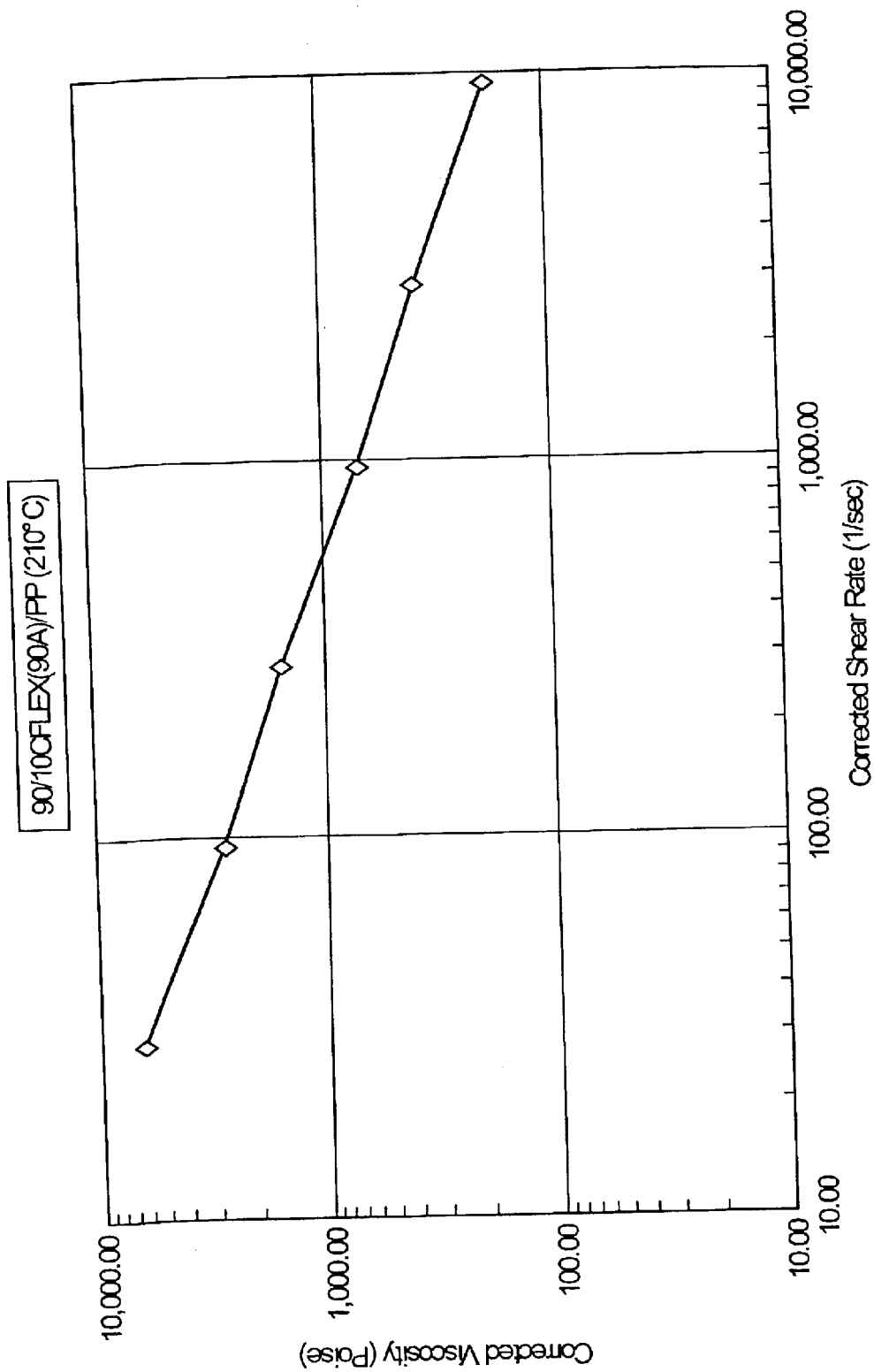
FIG. 4 shows the rheological properties (i.e., viscosity versus shear rate) of a thermoplastic elastomer sold under the trademark of C-FLEX™ blended with polypropylene at a weight percent ratio of 90/10.
Figure 5:
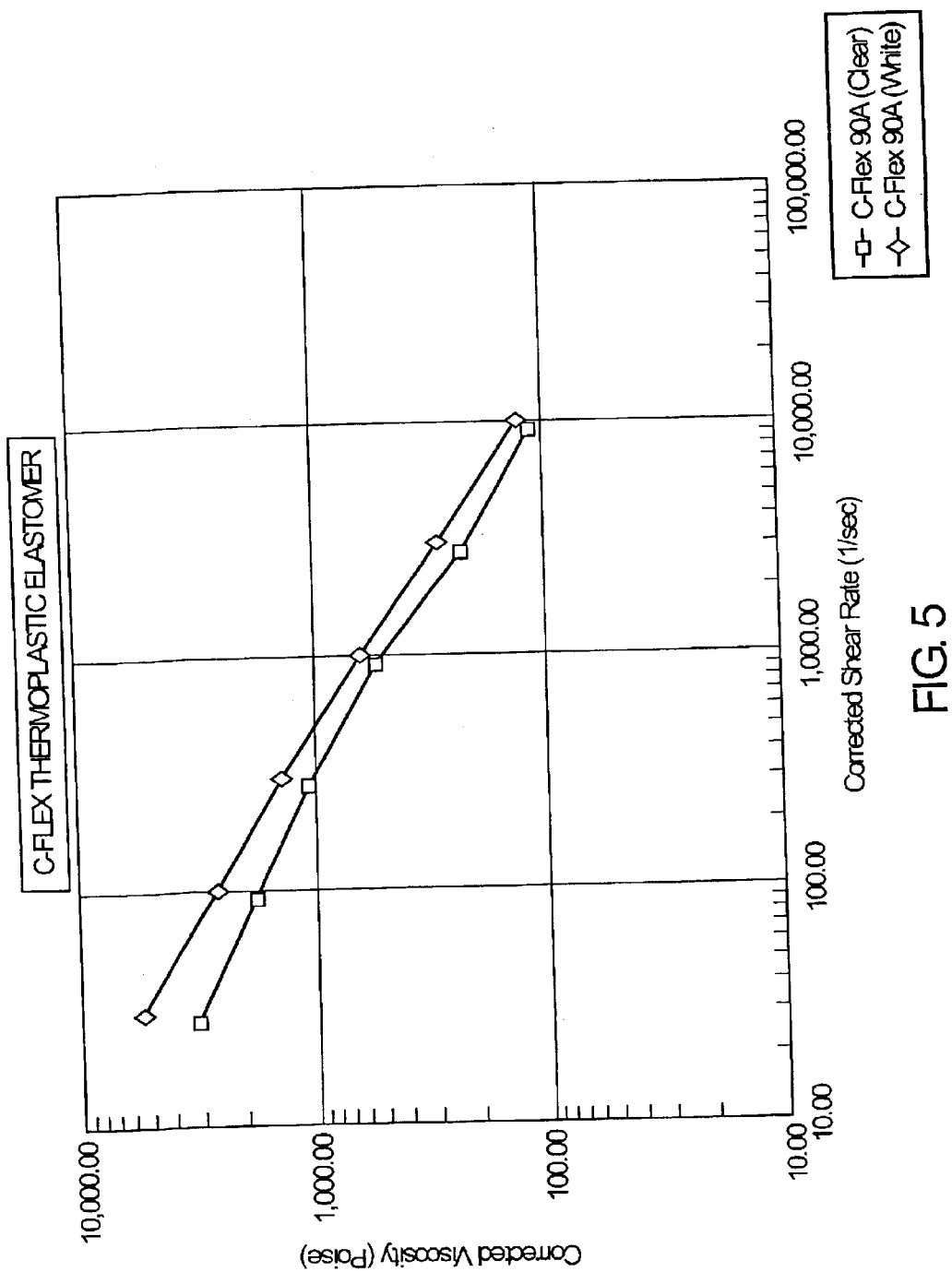
FIG. 5 shows the rheological properties (i.e., viscosity versus shear rate) of a thermoplastic elastomer sold under the trademark of C-FLEX™.

A variety of materials may be used to practice the invention. Material selection for the hub and the tube is based upon several factors such as Theological properties (i.e., viscosity vs. shear rate), flexural modulus, the hardness of the material, and melt flow. As shown in FIGS. 1–6, the materials should be selected wherein the slope of the viscosity and shear rate is approximately the absolute value of 1.0 poise·seconds or greater. For example, FIG. 1 shows the rheological properties of polypropylene. FIG. 1 further provides a slope of −0.433. FIG. 2 shows the Theological properties of a thermoplastic elastomer sold under the trademark of C-FLEX™ blended with polypropylene. There is a 80/20 by weight ratio of C-FLEX™ to polypropylene. FIG. 2 further provides a slope of −3.16. FIG. 3 shows the Theological properties of a thermoplastic elastomer sold under the trademark of C-FLEX™ blended with polypropylene. There is approximately a 85/15 ratio by weight of C-FLEX™ to polypropylene. FIG. 3 further provides a slope of −0.82. FIG. 4 shows the rheological properties of a thermoplastic elastomer sold under the trademark of C-FLEX™ wherein the ratio by weight of C-FLEX™ to polypropylene is approximately 90/10. FIG. 4 further provides a slope of −2.49. FIG. 5 shows the rheological properties of a thermoplastic elastomer sold under the trademark of C-FLEX™. FIG. 5 further provides slopes of approximately −1.54 and −2.26. It is preferable to use C-FLEX™ (90A) or Santoprene® (Theological properties not shown in FIG. 5). Melt flow that is highly shear sensitive is preferred as shown by a steep slope such as a slope of an absolute value of 1 or greater.

Figure 6:
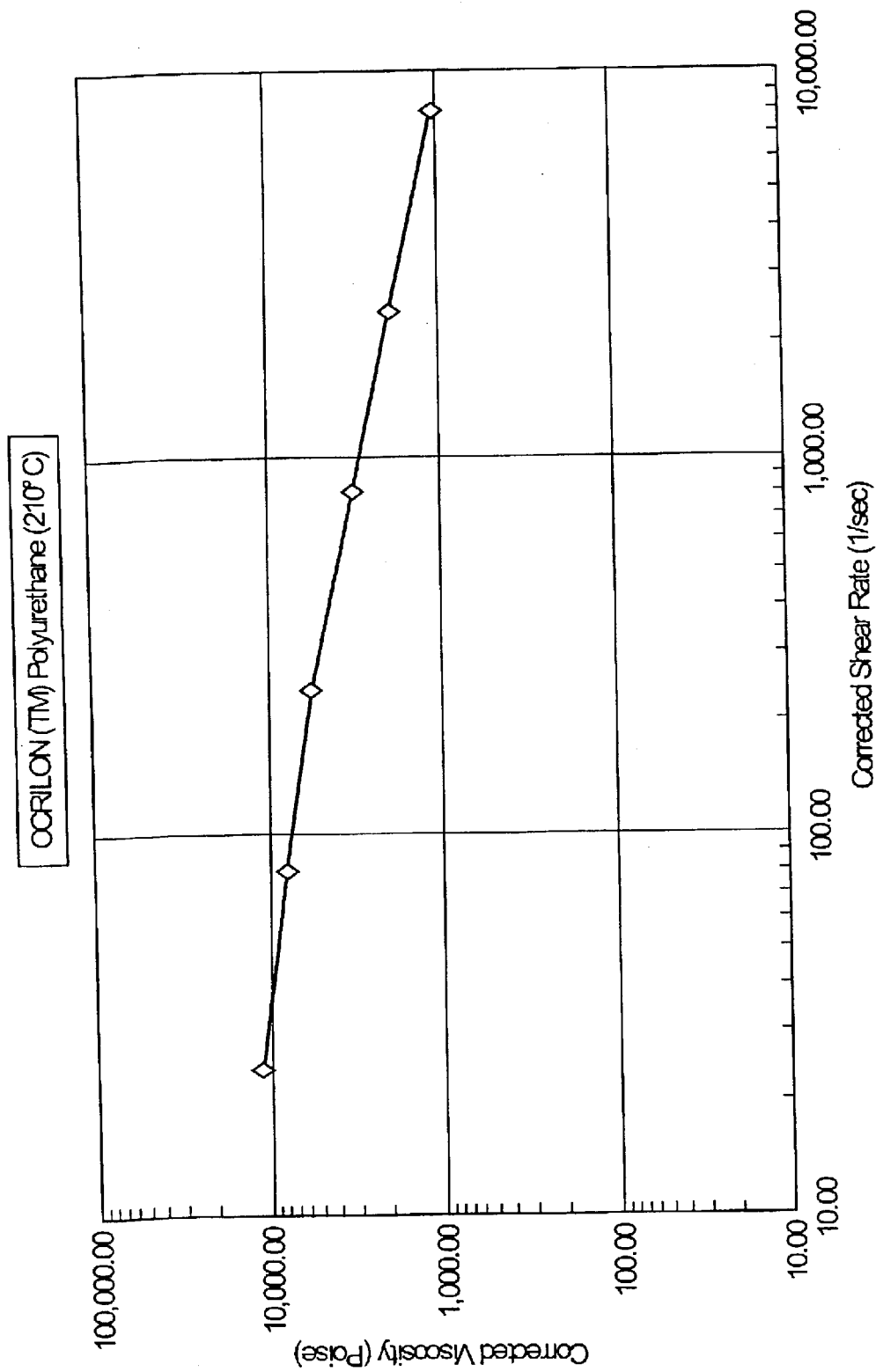
FIG. 6 shows the rheological properties (i.e., viscosity versus shear rate) of OCRILON™ polyurethane.

FIG. 6 shows the rheological properties of a polyurethane available under the trademark of OCRILON™ polyurethane (a proprietary polyurethane of Johnson & Johnson Medical). The slope in FIG. 6 is −6.7.

Table 1 provides a summary of some of the slopes taken from the curves presented in FIGS. 1–6.

TABLE 1

Shear Sensitivity of Selected Polymers
Summary of Slope Data

| Type | Polymer | Temperature (° C.) | Slope |
|---|---|---|---|
| Nylon | ULTRAMID B3 ™ | 250 | −0.003 |
| Polypropylene | polypropylene | 210 | −0.433 |
| Polypropylene Blends | 80/20 C-FLEX ™/ polypropylene | 210 | −3.16 |
| | 85/15 C-FLEX ™/ polypropylene | 210 | −0.82 |
| | 90/10 C-FLEX ™/ polypropylene | 210 | −2.49 |
| | 90/10 C-FLEX ™/ polypropylene | 175 | −7.8 |
| Thermoplastic Elastomer | C-FLEX ™ 90A (Clear) | 210 | −1.54 |
| | C-FLEX ™ 90A (White) | 210 | −2.26 |
| ABS/Polyurethane Blend | PREVAIL ™ 3050 | 230 | −0.073 |
| | | 220 | −0.61 |
| | | 210 | −1.95 |
| Elastomeric Polyamides | Polyetheramide (PEBAX ™) | 265 | −5.56 |
| | | 250 | −5 |
| Polyurethane | OCRILON ™ | 210 | −6.7 |

In addition to rheological properties, the flexural modulus of the material is considered in selecting a polymer. The flexural modulus of the catheter tubing that is fabricated should be approximately 50,000 psi or higher when the catheter tubing is dry and less than 35,000 psi when the catheter tubing is hydrated. A flexural modulus approximately in the range of 25,000 psi and below is preferred for a catheter tubing that is hydrated and 85,000 psi to 150,000 psi is preferred for a catheter tubing that is dry.

The hardness of the material is also considered in selecting a polymer. Materials exhibiting a hardness approximately in the range of 40 to 75 shore D is preferable.

Examples of the types of conventional materials that may be used in this molding process for the hub include:

polyolefins such as polyethylene, polypropylene, TEFLON™ and fluoro-olefinic copolymers such as fluorinated ethylene propylene copolymer (FEP), and blends thereof;

polyamides, polyetheramides, polyesteramides and blends thereof;

polyesters;

polyurethanes such as OCRILON™ resin, a proprietary optically clear radiopaque polyurethane from Johnson & Johnson Medical located in Arlington, Tex.; TECOFLEX™ and TECOTHANE™ commercially available from Thermedics, Inc. located in Woburn, Mass. and blends of OCRILON™ resin, TECOFLEX™ and TECOTHANE™;

polycarbonate-based polyurethanes such as CARBOTHANE™ commercially available from Thermedics, Inc., located in Woburn, Mass. and blends of OCRILON™, TECOFLEX™, and TECOTHANE™.

Synthetic thermoplastic elastomers (e.g., polyolefins filled with styrene-ethylene, butylene-styrene block copolymer and polydimethyl siloxane, etc.), an example of which is commercially available as C-FLEX™ from Consolidated Polymer Technologies, Inc. located in Largo, Fla.; Santoprene® thermoplastic rubber (highly cross-linked rubber particles dispersed throughout a continuous thermoplastic matrix); commercially available from Advanced Elastomer Systems, Akron, Ohio; etc.

Acrylonitrile-butadiene-styrene (ABS) polyurethane blends such as PREVAIL™ commercially available from Dow Chemical, Plastics Division, located in Midland, Mich.;

Liquid crystal polymers (e.g. 2-napthalene carboxylic acid, 6-(acetyloxy) polymer with 4 (acetyloxy) benzoic acid, aromatic liquid crystal polyester, etc.) commercially available as VECTRA™ from Ticona, a division of Hoechst (Summit, N.J.) and XYDAR™ from Amoco Polymers, Inc. located in Alpharetta, Ga.;

Nylons (e.g., commercially available as ULTRAMID $B_3$™ Nylon 6, and fiberglass reinforced nylon 6 commercially available from BASF Corporation located in Wyandotte, Mich.

Polyether nylons such as PEBAX 6333™ and PEBAX 2533™ commercially available from Elf Atochem North America, Inc. located in Philadelphia, Pa.

Although this list of compounds provides types of materials that generally may be used with the process described herein, it is to be appreciated that the invention is not limited to these compounds and other like or similar compounds or materials may also be used.

The preferred hub material to be used is C-FLEX™ and Santoprene® thermoplastic elastomer. With this type of material, the preferred barrel temperature range is 175–300° C. and a preferred range of gas pressure used is 1,000–4,000 psi. It will be appreciated that the barrel temperature for some of the materials listed above may reach above 300° C. For example, liquid crystal polymer may be heated to 350° C.

Selection of Material for Tube

The preferred materials that may be used for forming the tube include Teflon™ (e.g. fluorinated ethylene propylene copolymer), polyurethanes, rubber-filled polyolefins such as C-FLEX™ and Santoprene® thermoplastic elastomer. It will be appreciated that radiopacity inducing agents such as tungsten, barium sulfate, bismuth compounds and other suitable compounds may be combined with the tube materials. Radiopacity inducing agents permit a healthcare worker to locate a tube in a body in case the tube is broken and moves to a different location in the body. In the embodiment in which a one-piece catheter is produced from a single material, an optimum material is selected from any one of the materials listed above for the hub or for the tube except liquid crystal polymers.

Equipment

Molding machines that are most appropriate to practice the invention have high speed/low pressure injection capabilities such as the NIIGATA NN35MI™ machine commercially available from Daiichi Jitsugyo (America) located in Itasca, Ill. and equipped with a shut-off valve may be used with this and other machines. These machines are generally equipped with two sets of different sized injection cylinders that are symmetrically located and are diagonally opposed to each other and are on either side of the injector device. Injection molding machines use effective size (e.g. volume of the chamber as defined by length and the inner diameter of the cylindrical chamber) of the hydraulic injection cylinder as a pressure control with the flow control valve substantially open. A single cavity tool should use the high speed/low pressure injection molding machine with a low clamping tonnage such as in the range of 15 and 50 tons. A screw diameter of 18 mm is preferred. The shot size used should be less than 4.0 ounces. For multi-cavity tooling, a large tonnage (e.g., up to 150 tons) machine may be required with shot sizes larger than 4 ounces. Other conventional machines with shut-off valves are also suitable for this process.

In conjunction with injection molding machine, gas assist machines are used, such as the Bauer programmable NCU (Bauer Compressors located in Norfolk, Va.). Preferred gas assist machines are those that are capable of controlling multiple gas pressure phases.

Cavity Dimensions

The cavity size varies with the gauge of the catheter tube to be fabricated. For example, the outer diameter of the catheter tube made by the invention includes large 12 gauge such as 0.112 inches to small 26 gauge such as 0.0216 inches. The inner diameter of the catheter tube ranges from 0.1 to 0.021 inches. The length of the tube ranges from 2½ to ½ inches. The hub has an inner diameter that ranges from 0.159 inches to 0.179 inches and an outer diameter that ranges from 0.31 inches to 0.32 inches. Table 2 provides some examples of the specifications of different catheter tubes. However, it will be appreciated that other dimensions may also be used to practice the invention.

TABLE 2

Examples of Dimensions of Fabricated Tubes ((millimeters) (mm))

| Outer Diameter Of Tube | Inner Diameter Of Tube | Length Of Tube | Wall Thickness Of Tube | Gauge |
|---|---|---|---|---|
| 2.13 | 1.75 | 31 | 0.19 | 14 |
| 2.13 | 1.75 | 56 | 0.19 | 14 |
| 1.70 | 1.38 | 31 | 0.16 | 16 |
| 1.70 | 1.38 | 56 | 0.16 | 16 |
| 1.28 | 0.98 | 44 | 0.15 | 18 |
| 1.28 | 0.98 | 31 | 0.15 | 18 |
| 1.10 | 0.80 | 31 | 0.15 | 20 |
| 1.10 | 0.80 | 25 | 0.15 | 20 |
| 1.10 | 0.80 | 44 | 0.15 | 20 |
| 0.83 | 0.63 | 25 | 0.10 | 22 |
| 0.70 | 0.50 | 19 | 0.10 | 24 |

Figure 7:
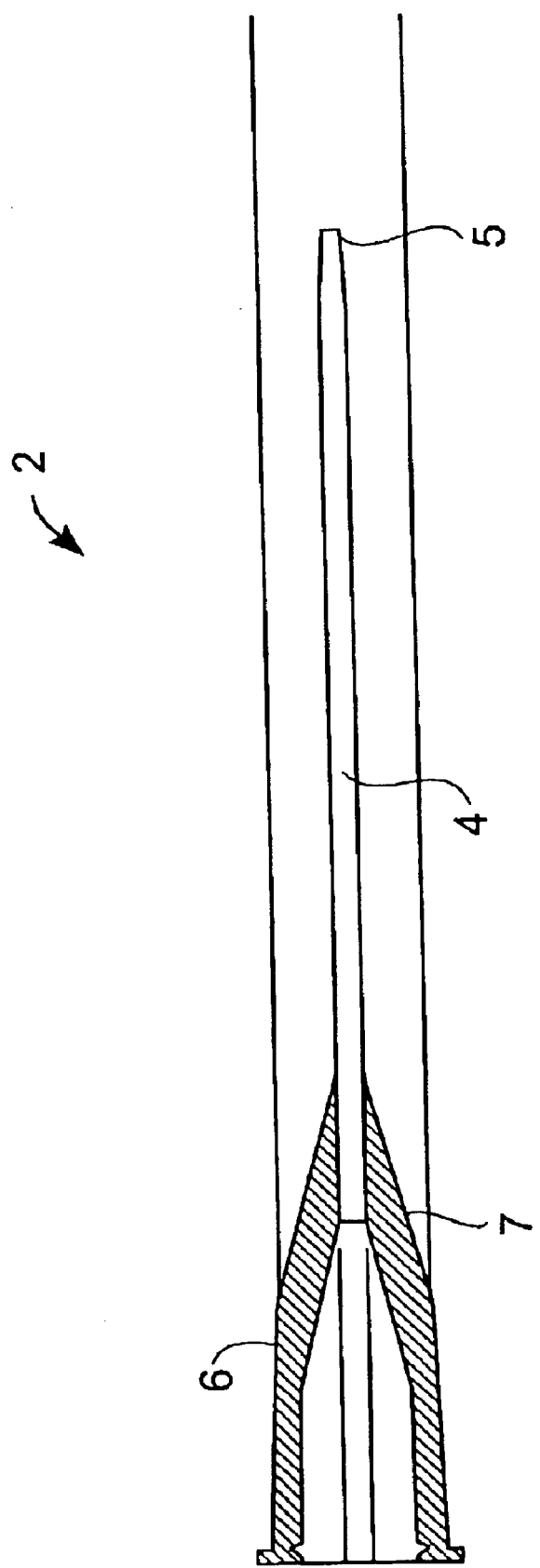
FIG. 7 shows a one-piece catheter device that is formed by practicing the invention.

FIG. 7 shows a one-piece catheter device 2 that is formed by practicing the invention. The one-piece catheter device has a tube portion 4 and a hub portion 6. It will be appreciated that tube portion 4 of the catheter device 2 is hollow therethrough. This hollow central portion is formed by gas assist injection molding. The hub portion is hollow in the central portion of the hub portion 6. At the distal end of hub portion 6 is nose 7. Nose 7 transitions into tube portion 4. Tube portion 4 ends with a tapered bevel 5 at the distal end of tube portion 4.

Figure 8:
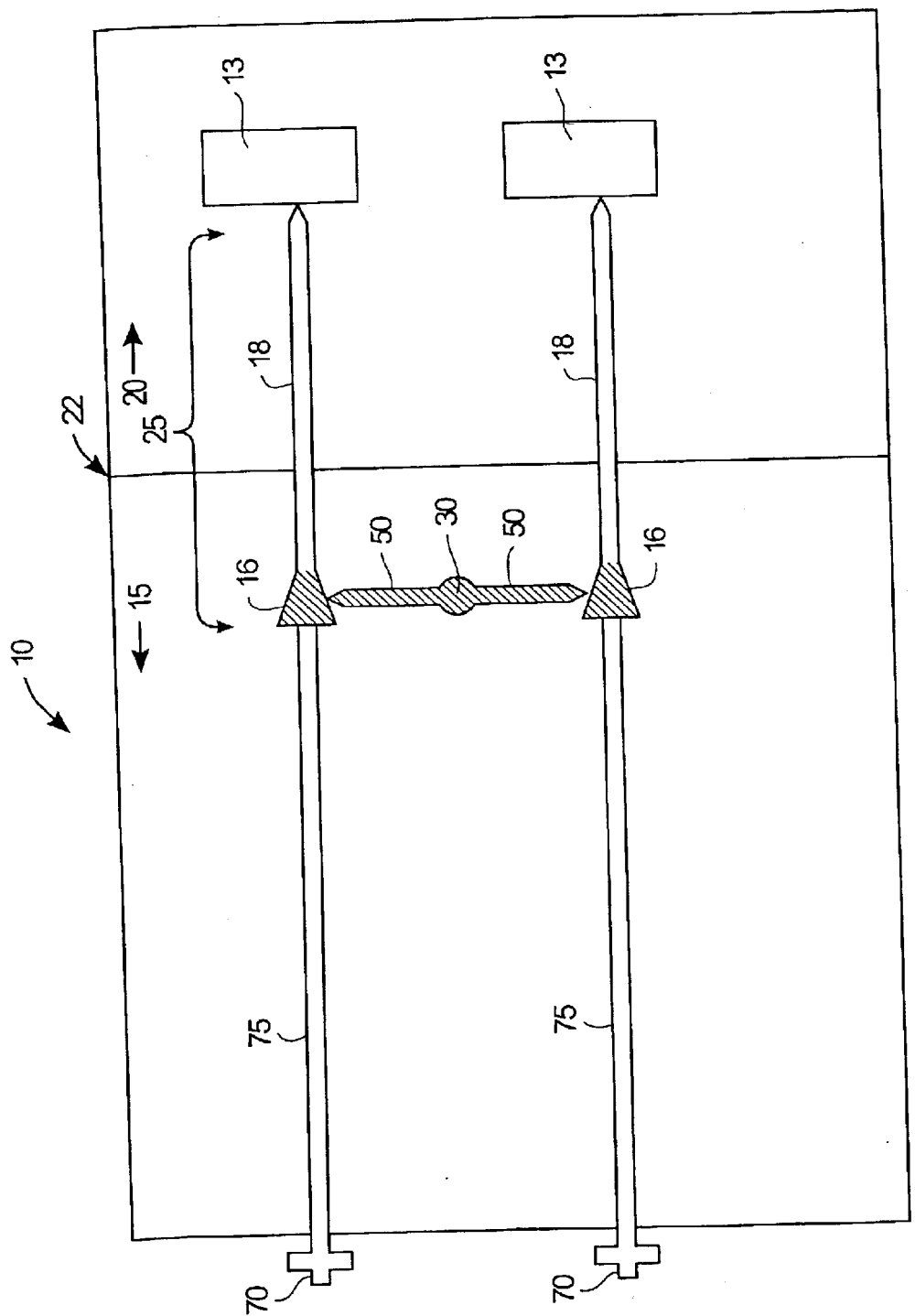
FIG. 8 shows a top view of a mold used to form an intravascular device in accordance with an embodiment of the invention.

FIGS. 8–12 show one embodiment of the invention wherein injection molding is used and a fluid such as inert gas (e.g., nitrogen, air, helium, argon, etc.) is introduced through the hub portion of the mold to assist in forming the one-piece catheter hub component. Because the molten polymer enters the hub portion of the cavity, the hub is generally formed first followed by the formation of the tube. C-FLEX™ and Santoprene® thermoplastic elastomer, used under the operating conditions provided below, is generally capable of overcoming the known limitation of having an aspect ratio >200 but yet still capable of providing a reliable product. FIG. 8 shows one-half of the mold used in manufacturing a one-piece catheter hub component. A second half (not shown) [first half (15) and second half (20)] is mated with the illustrated half to form mold 10. Pressure may be applied to the first half 15 against second half 20, to second half 20 against first half 15 or to both halves simultaneously to ensure that cavity 25 is tightly fitted or formed. Cavity 25 has a first portion that provides a tube and a second portion that provides a hub.

Mold 10 has an inlet 30 that allows molten polymer to enter mold 10. The molten polymer such as C-FLEX™ and/or Santoprene® thermoplastic elastomer is introduced to mold 10 at a pressure in the approximate range of 4,390 psi to 40,000 psi. Additionally, the molten polymer is generally maintained at a temperature that ranges from 175° C. to 220° C. It will be appreciated that other pressures and temperatures are possible depending upon the material used. The polymer then moves along runner 50 in the direction of hubs 16.

The two halves (15 and 20) meet at split line 22. At split line 22, inlet for fluid flow is not open for fluids such as nitrogen gas, air, helium, argon, etc. to enter mold 10. FIG. 8 further shows the feed material such as a polymer spreading from runner 50 to hub 16 for both devices.

Figure 9:
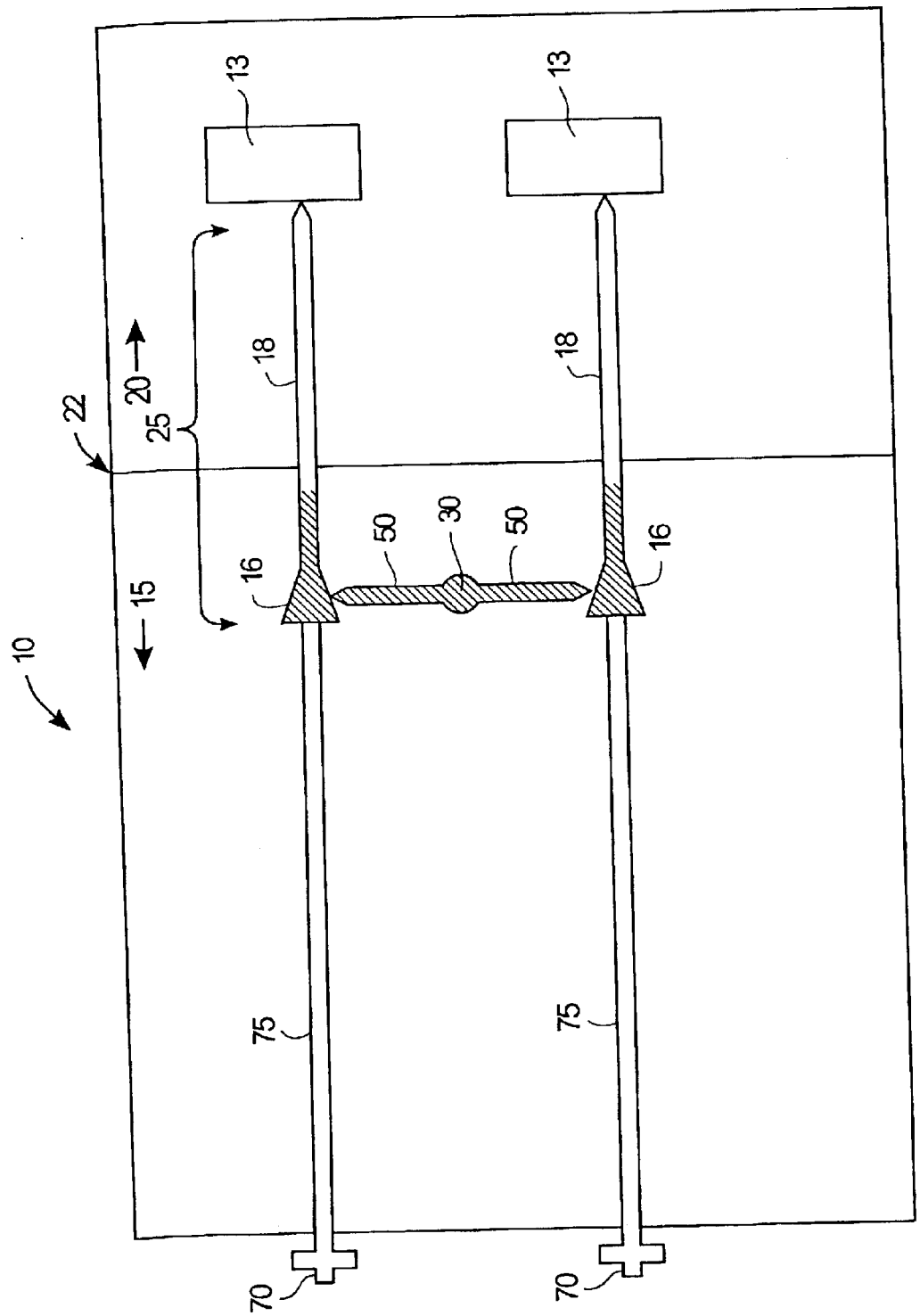
FIG. 9 shows the mold of FIG. 8 wherein molten material is injected into the mold though the hub side of the cavity.

FIG. 9 shows the same mold as FIG. 8 wherein a layer of the polymer forms on the cavity surface and begins to solidify. The solidified polymer covers a larger surface of the cavity compared to the solidified polymer shown in mold 10 of FIG. 8. The quantity of polymer introduced into cavity 25 is controlled to a small quantity to allow the fluid to advance the polymer further into the cavity surface of mold 10.

Figure 10:
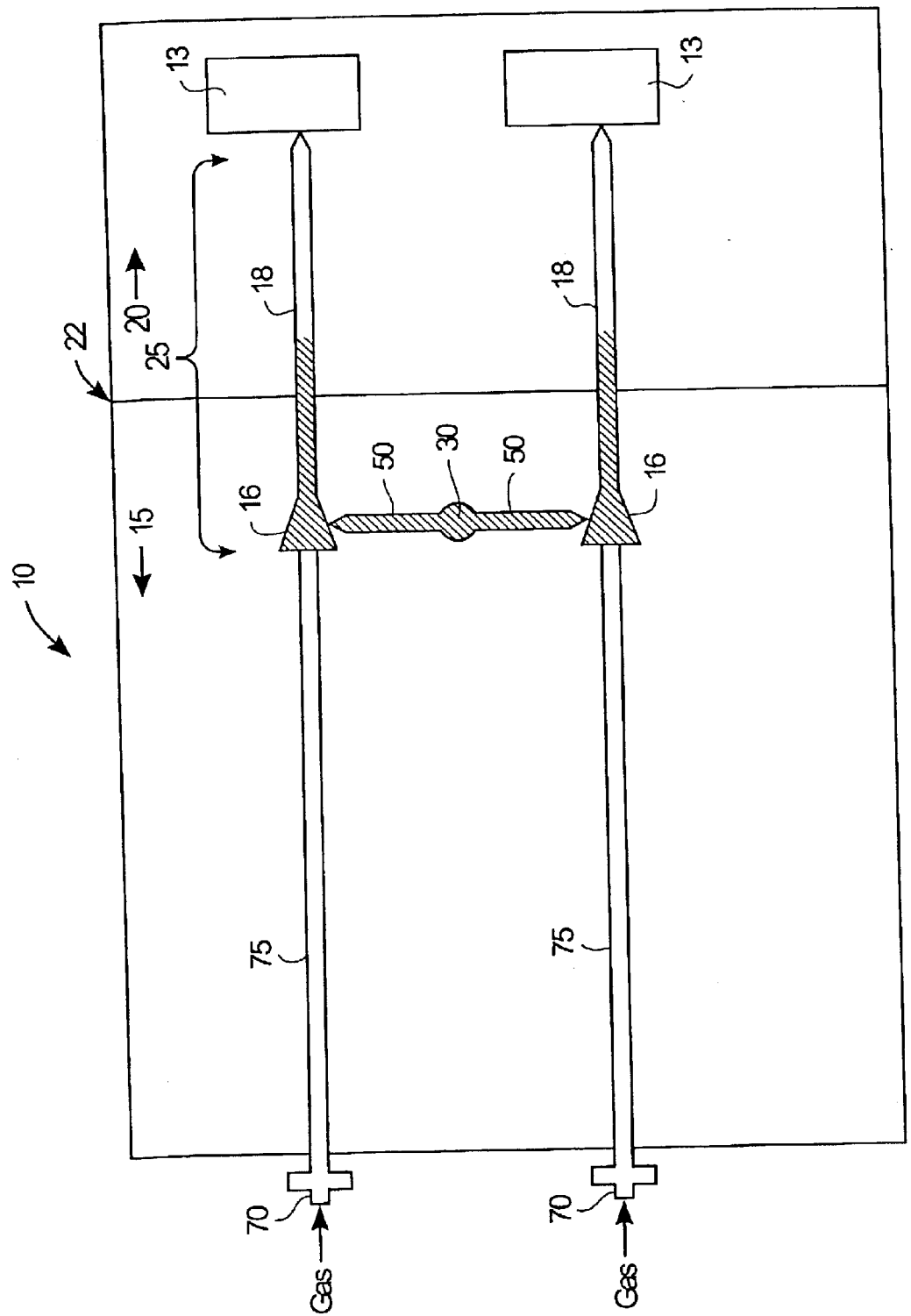
FIG. 10 shows the mold of FIG. 8 wherein a fluid such as a gas enters the mold in order to cause the polymer to move through the hub side of the cavity.

FIG. 10 shows a fluid such as gas (e.g. nitrogen gas, air, helium, argon, etc.) entering inlet 70 for mold 10. The gas is introduced from a low pressure of 500 psi to as high as 9,000 psi when gas is introduced during the injection molding process. As the gas passes through tube 75, pressure builds at the proximal end of hub 16 behind the polymer that was injected. This pressure causes the polymer to move in the distal direction of tube cavity 18. It will be appreciated that although gas is shown to be introduced after the polymer is fed into the cavity, the gas may be introduced simultaneously or about the same time as the molten polymer is fed into the cavity.

Figure 11:
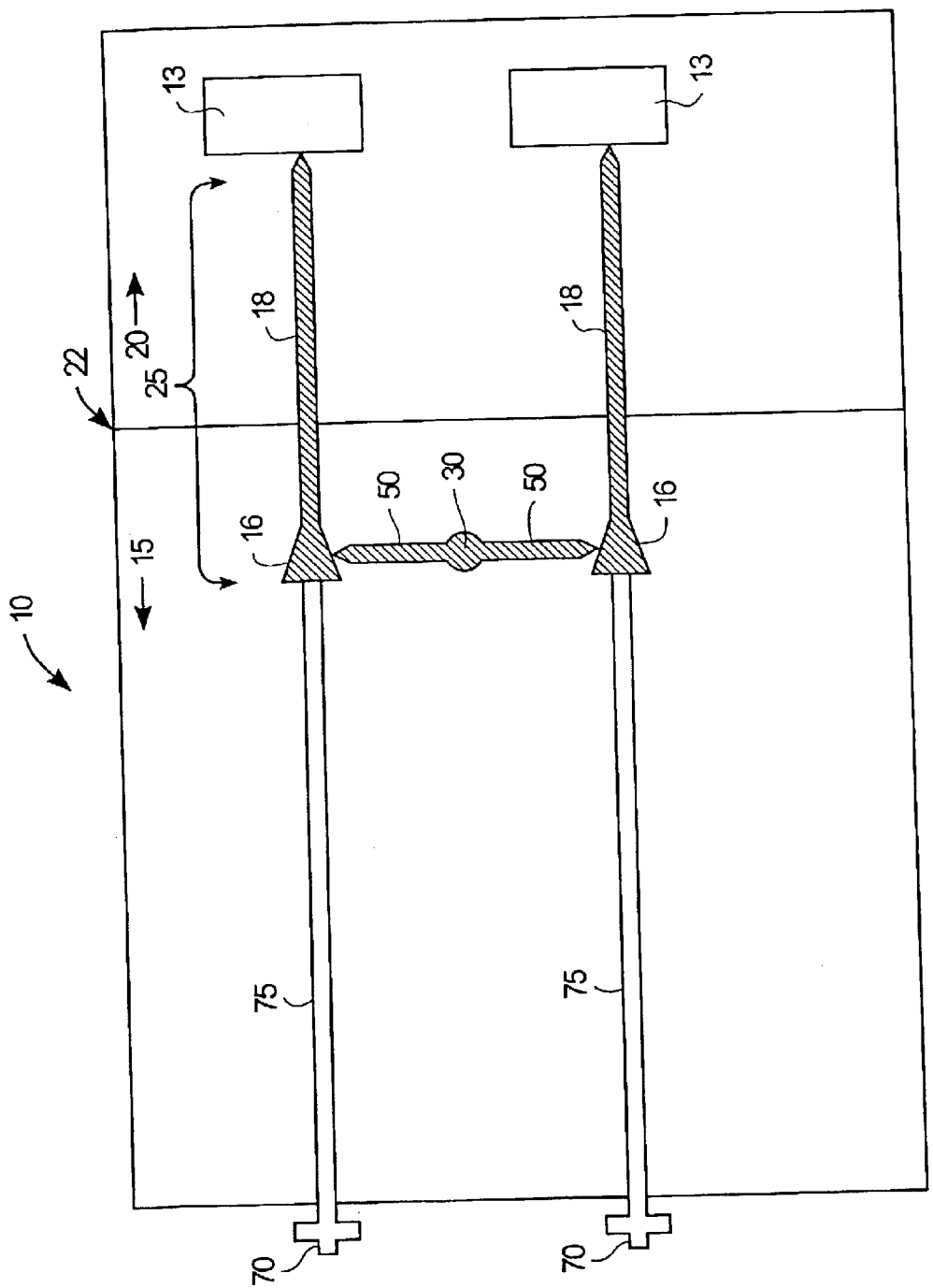
FIG. 11 shows the mold of FIG. 8 filled with molten material and with a hollow channel formed by the passage of gas through the cavity.

FIG. 11 shows mold 10 having hub 16 and tube 18 filled with polymer but with a hollow channel formed in the tube by the gas. The process of filling cavity 25 generally takes 0.5 to 5 seconds. Excess polymer exits an exit channel into a spillover area 13 of the mold. Alternatively, the precise amount of material is used and no polymer is considered excess. This is accomplished by measuring the amount of necessary polymer through applying a short-shot of material into the mold. The amount of polymer used is adjusted until the amount necessary to prevent spillover is determined by adjusting the amount of polymer introduced into cavity 25.

Figure 12:
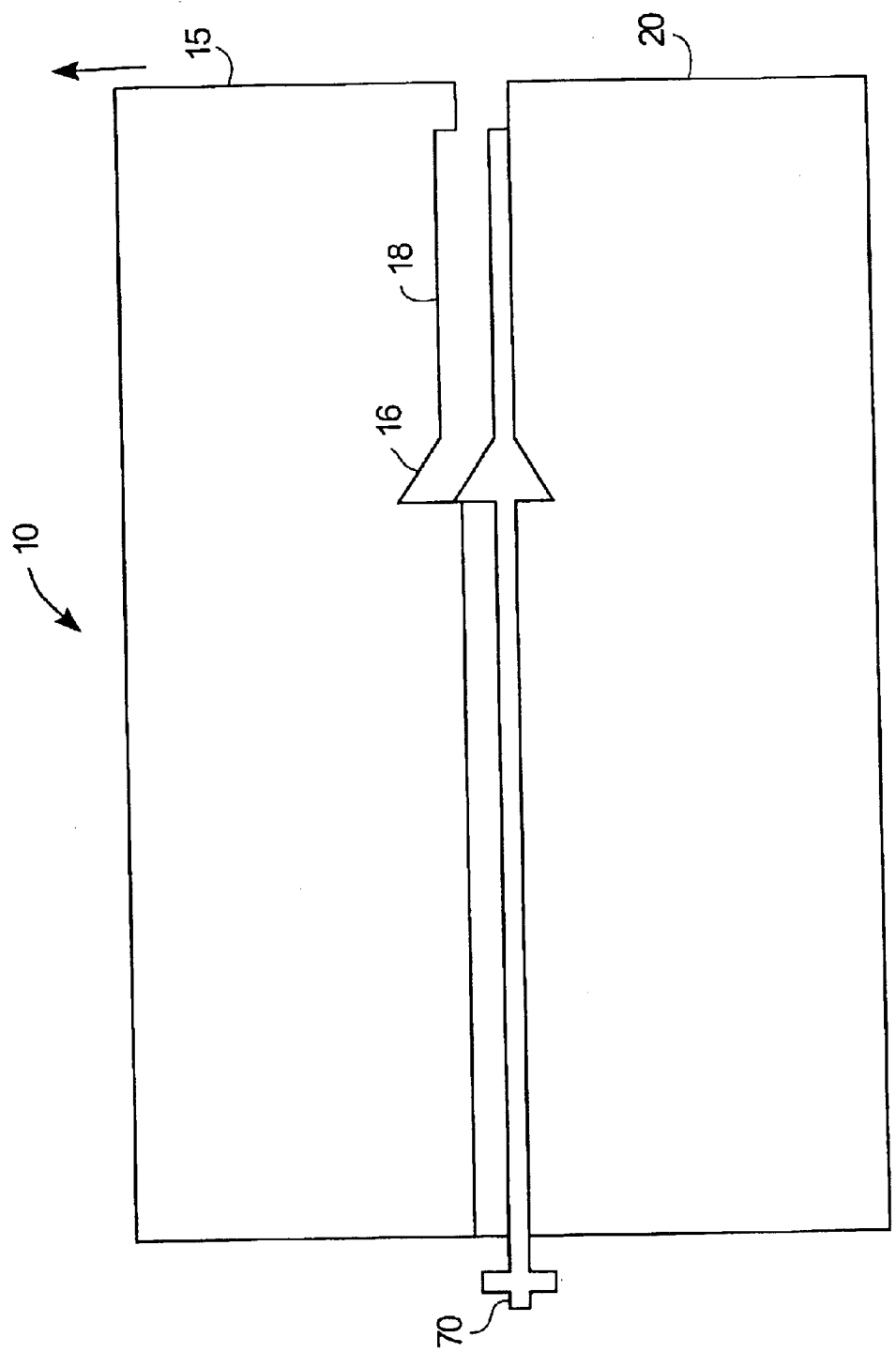
FIG. 12 shows a cross-sectional view of the mold of FIG. 8 wherein the first half and second half of the mold are separated.

After the polymer has begun to solidify, FIG. 12 shows mold 10 wherein first half 15 is separated from second half 20. It will be appreciated that first and second halves (15 and 20) may be mated longitudinally or vertically. The single integral piece may then be removed or ejected by a mechanism in the mold (not shown). The process cycle represented by FIGS. 8–12 may then be repeated. It will be appreciated that although FIGS. 8–12 show two devices being manufactured simultaneously, other devices such as a single device or more than two devices, i.e., multiple devices can be manufactured simultaneously or at approximately the same time.

Preferably, a portion of the mold forms the beveled end of a tube. In this embodiment of the invention, a polymer is injected into the hub portion of each of the hub cavities. The polymer then fills the tube portion and the bevel of each of the tube cavities.

Figure 13:
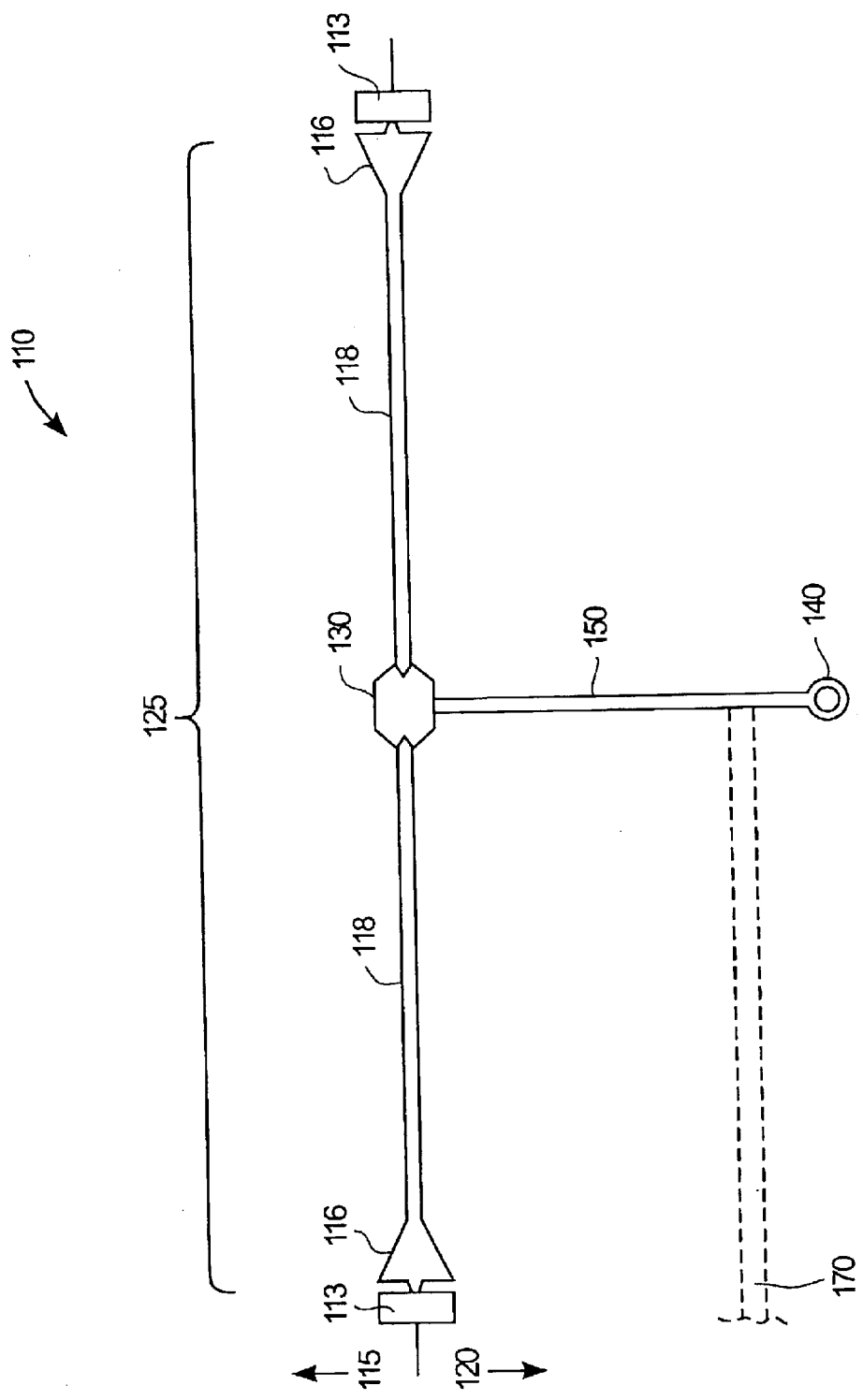
FIG. 13 shows a top view of a mold wherein a fluid is introduced through the tube of the catheter device in accordance with an embodiment of the invention.

FIGS. 13–17 show another embodiment on the invention wherein gas is introduced through the tube of the one-piece catheter and hub of mold 110. FIG. 13 shows a top view of mold 110 used to form a one-piece catheter and hub. FIG. 13 further shows a cavity portion for the hub 116 and the tube 118 for two devices. Material such as a polymer is heated until the temperature reaches the melt temperature of the polymer. The molten polymer then enters the tube side of the cavity at inlet 130 of mold 110. FIG. 13 further shows a gas pin 140 in communication with runner 150. Runner 150 communicates with the distal end of tube 118. FIG. 13 also shows spillover areas beyond hub 116 for the overflow of excess polymer.

Figure 14:
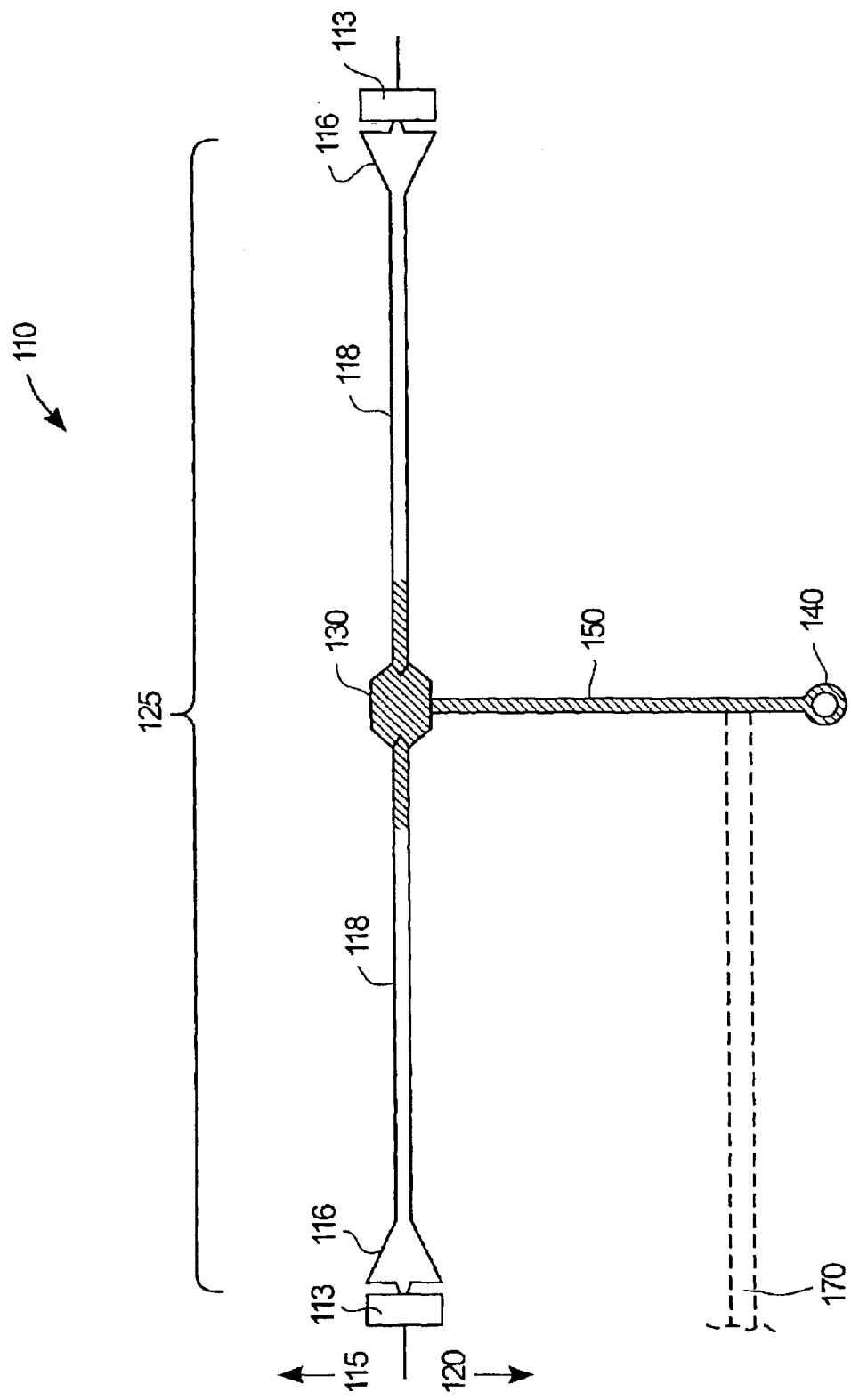
FIG. 14 shows molten material injected into two cavities for forming two catheters in accordance with an embodiment of the invention.

FIG. 14 shows the device of FIG. 13 with molten material entering inlet 130. The molten material begins to spread within cavity 125 for both devices. FIG. 14 further shows the molten polymer beginning to move in a proximal direction of tubes 118.

Figure 15:
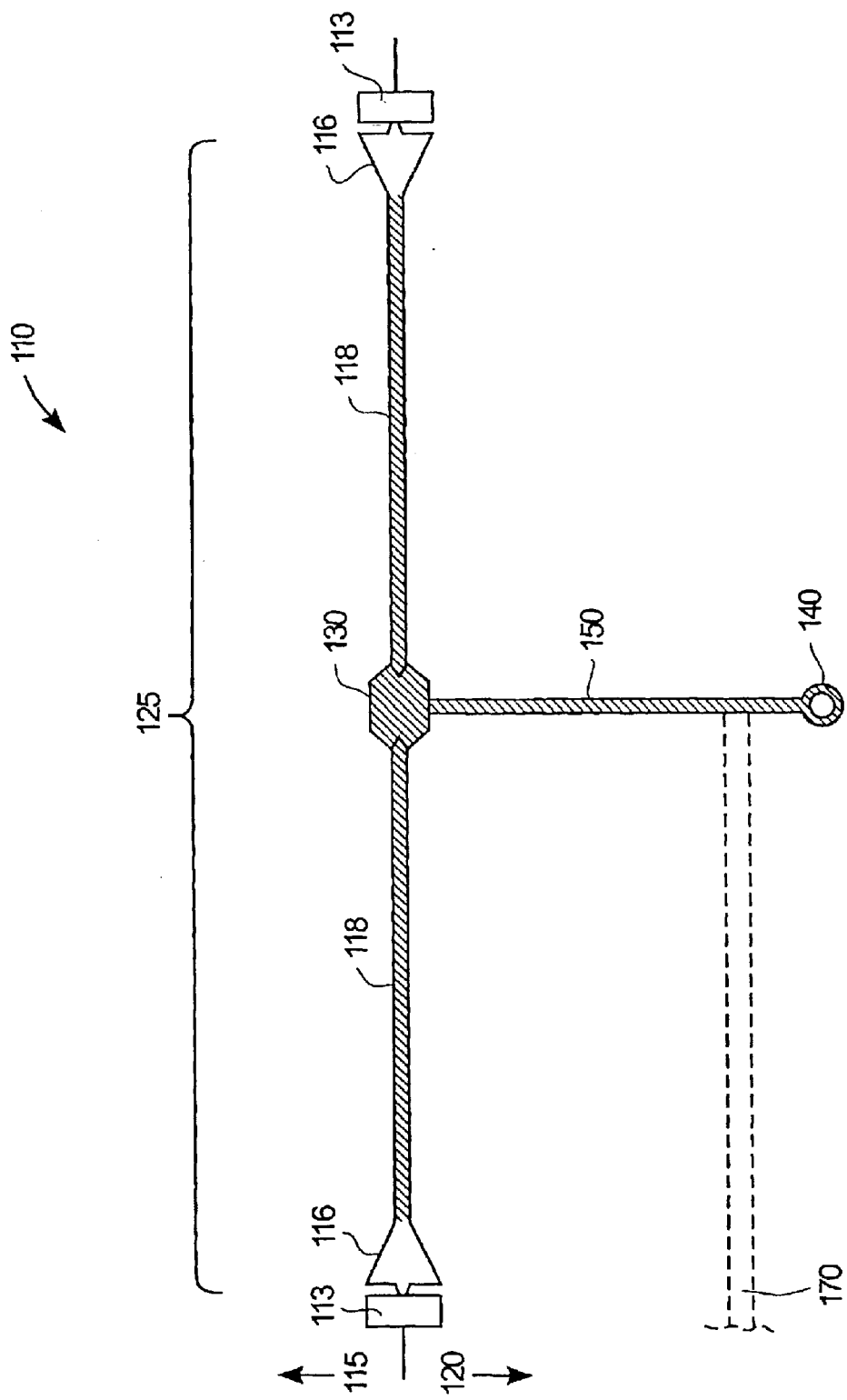
FIG. 15 shows molten material moving through the cavity tube of the catheter with the force of gas passing through the tube in accordance with an embodiment of the invention.

FIG. 15 shows that the polymer has continued to advance along tubes 118. Before the polymer fills cavity 125, the amount of polymer entering the cavity 125 is consumed. At this point, a fluid such as nitrogen gas, air, helium, argon, etc. enters inlet 170 and moves toward the general direction of runner 150 until the gas contacts the molten material. Upon contacting the molten material, the pressure begins to build behind the molten material and the gas pushes the molten material along the interior of cavity 125. The gas pressure is one of the contributing factors that causes the polymer to move through the remainder of the tube and hub cavity creating an interior channel throughout the cavity.

Figure 16:
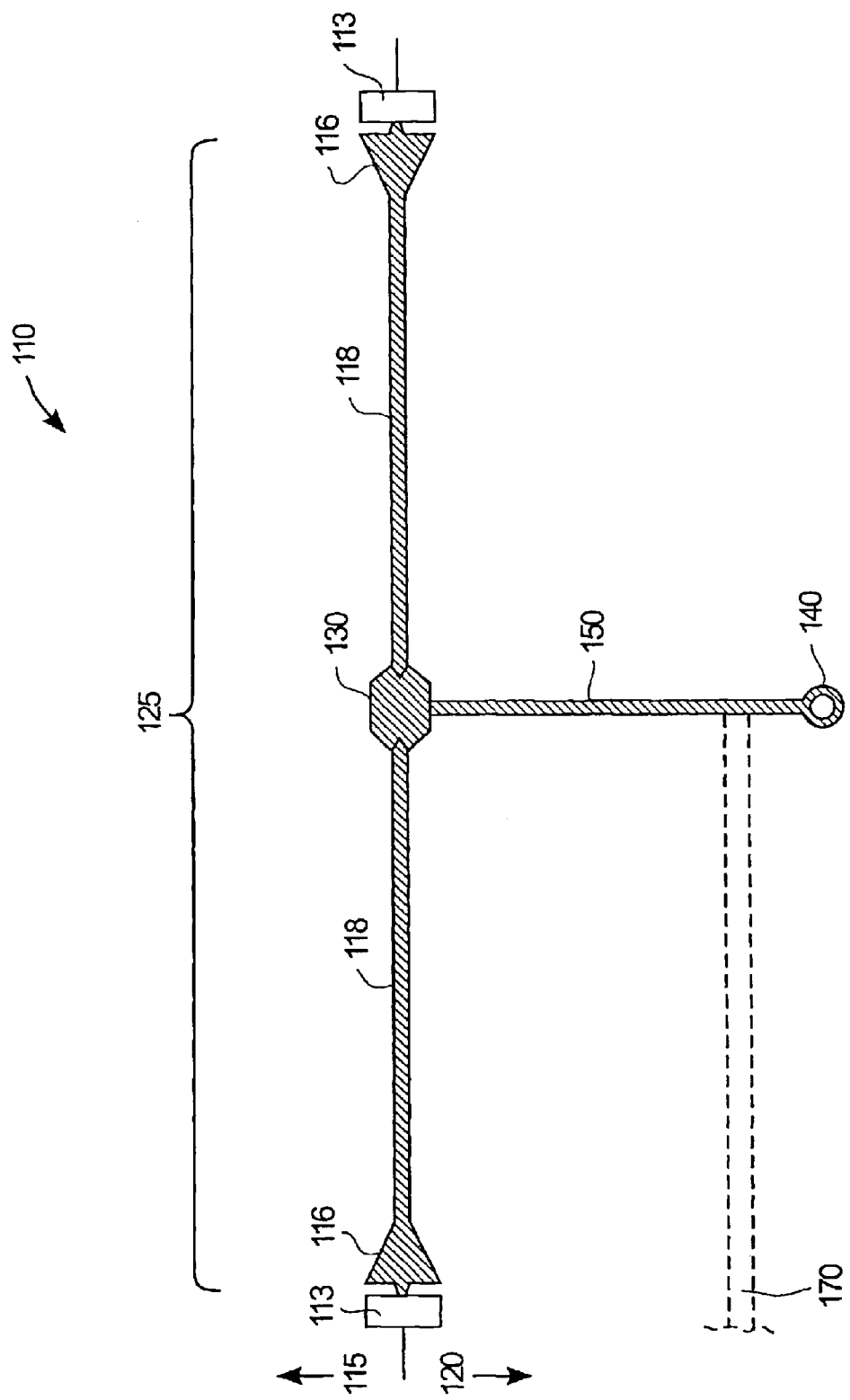
FIG. 16 shows that the molten material has filled the cavities of the mold and with a hollow channel formed by the passage of gas through the cavity in accordance with an embodiment of the invention.
Figure 17:
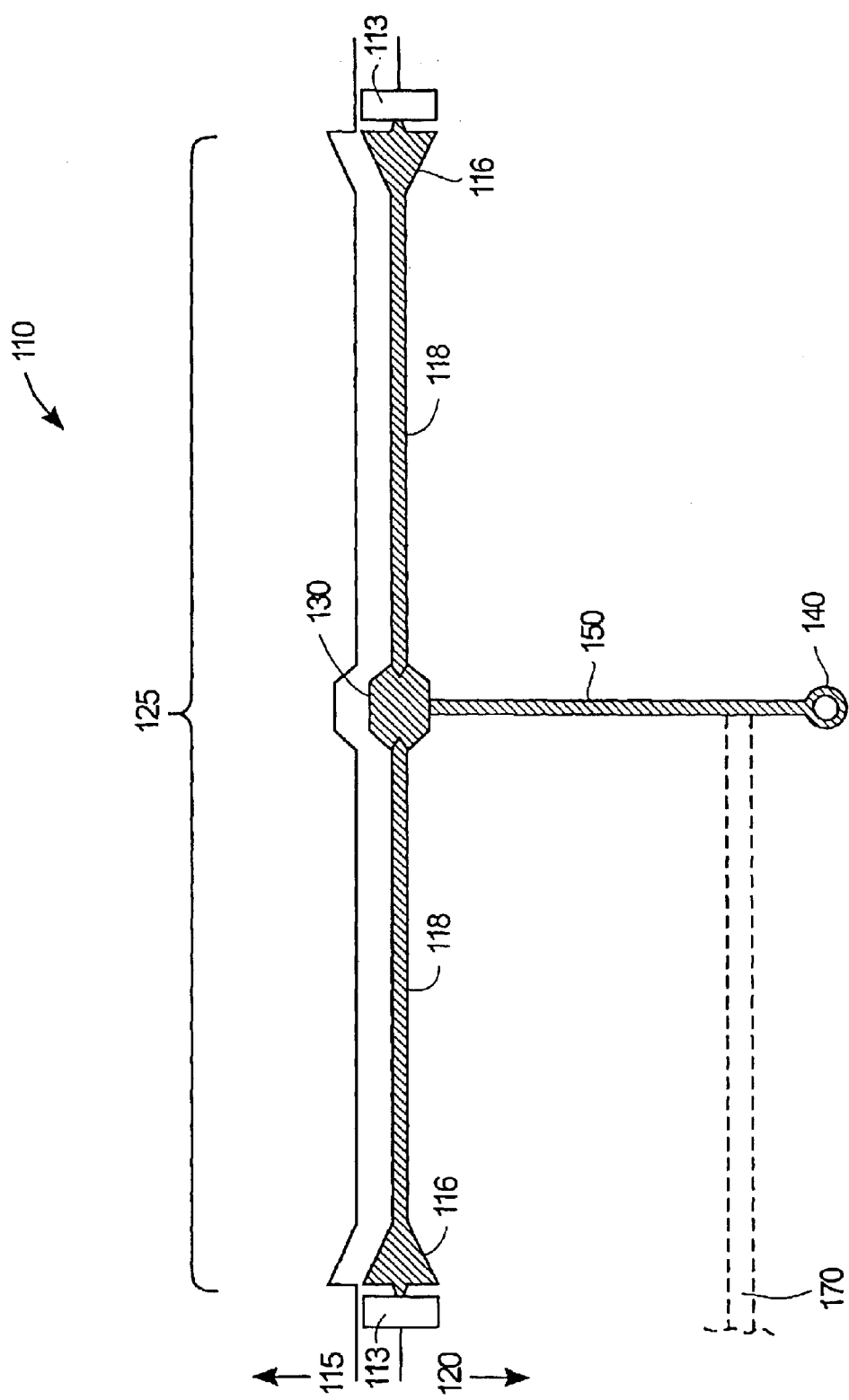
FIG. 17 shows the first half of the mold being separated from the second half of the mold in accordance with an embodiment of the invention.

FIG. 16 shows cavity 125 is filled with the polymer material but with a hollow channel formed in the tube by the gas. After a certain time period such as 3–20 seconds, the two halves of the mold are opened and the part is ejected. FIG. 17 shows first half 115 and second half 120 being separated thereby allowing the one-piece catheter tube and hub devices to be separated from mold 110. The process represented by FIGS. 13–17 may then be repeated.

FIGS. 18–29 show another embodiment of the invention wherein at least two portions of the one-piece catheter component comprise at least two different materials. A first portion of the intravascular device is made using one material. For example, mold 210 has a cavity for a hub in which the hub portion may be formed first. Mold 210 is then moved or cycled around by a rotating platen in the molding machine (not shown). A second material (or, alternatively, the same material) may be injected into a second cavity to form a second portion of the intravascular device such as a tube.

Figure 18:
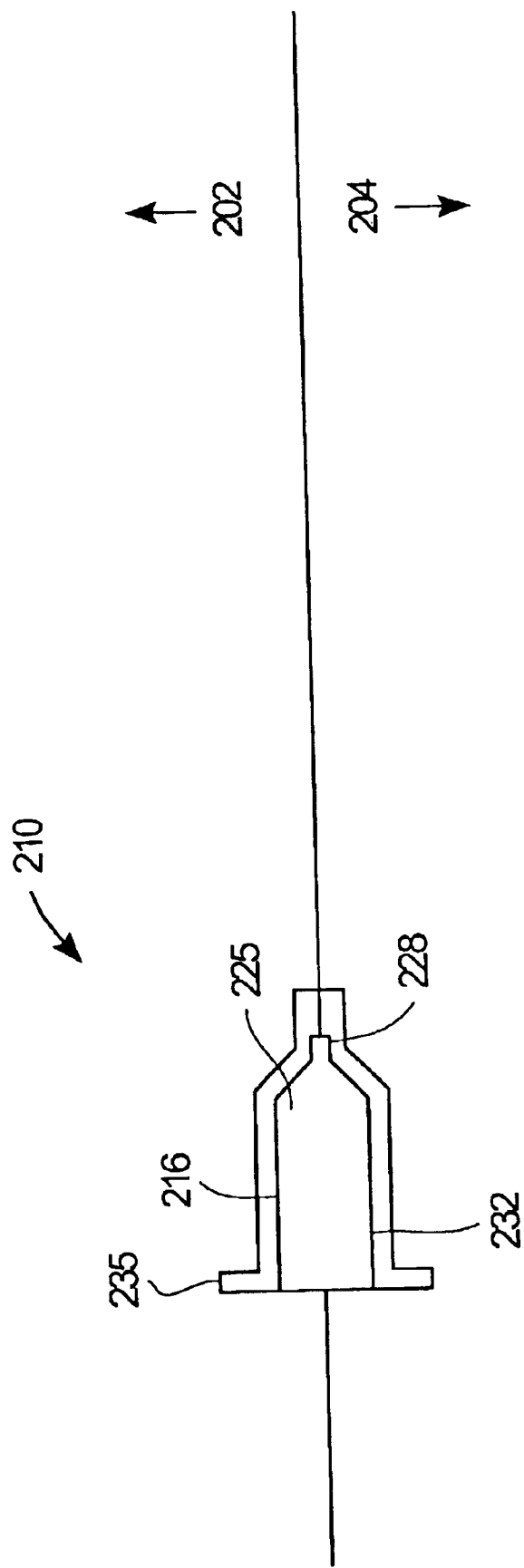
FIG. 18 shows a first portion of an intravascular device such as a hub that has a base or connector in accordance with an embodiment of the invention.

FIG. 18 shows a first portion of an intravascular device such as a hub 216 that has a base or connector 235.

Figure 19:
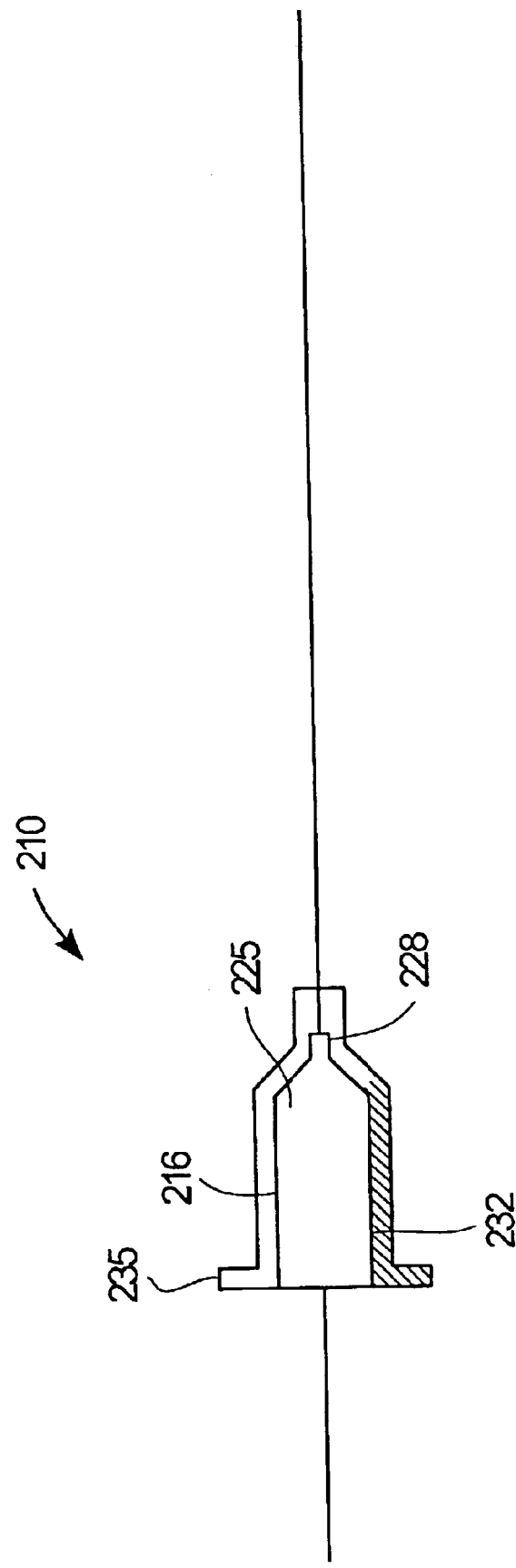
FIG. 19 shows the same mold as FIG. 17 except the molten polymer has been injected into a portion of the hub cavity and the polymer is beginning to solidify in accordance with an embodiment of the invention.

Connector 235 may be either a male or female luer lock. Nose 228 is formed at the end that opposes connector 235. The dimensions of the luer lock should conform to ISO International Standards 594/1 and 594/2. Nose 228 is subsequently coupled to a tube portion of the intravascular device. FIG. 18 further shows the location 232 of where the polymer may be fed into the hub cavity. It will be appreciated, however, that the inlet to the cavity for the hub for injecting molten polymer may be located anywhere along the hub cavity. For example, molten polymer may be fed in at location 225. FIG. 19 shows the same first mold 210 as in FIG. 18 except the molten polymer has been injected into a portion of hub cavity 216 and the polymer is beginning to solidify.

Figure 20:
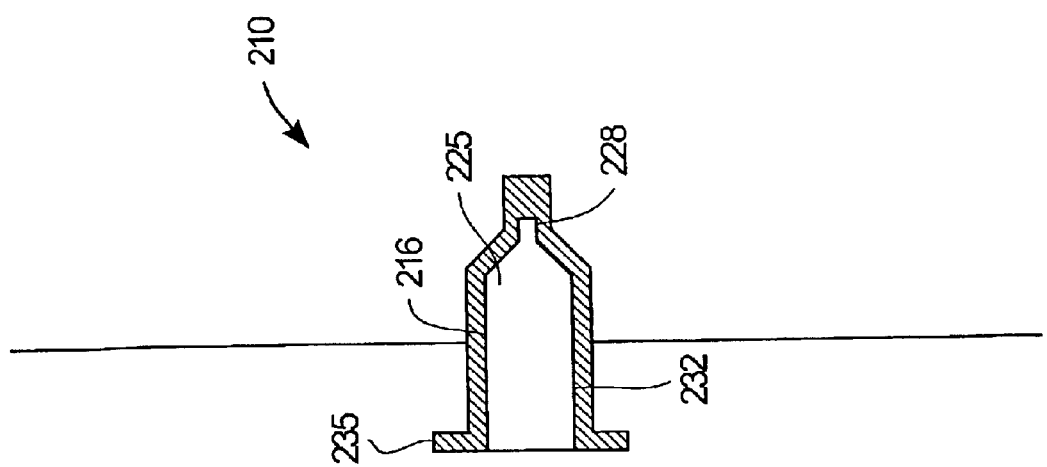
FIG. 20 shows the hub cavity filled with polymer in accordance with an embodiment of the invention.

FIG. 20 shows first mold 210 wherein the molten polymer has filled hub cavity 216 leaving a hollow central portion in the hub. This process generally takes 1–3 seconds. Although gas assist injection molding is not typically used with a hub cavity, this process could be used in forming nose 228.

Figure 21:
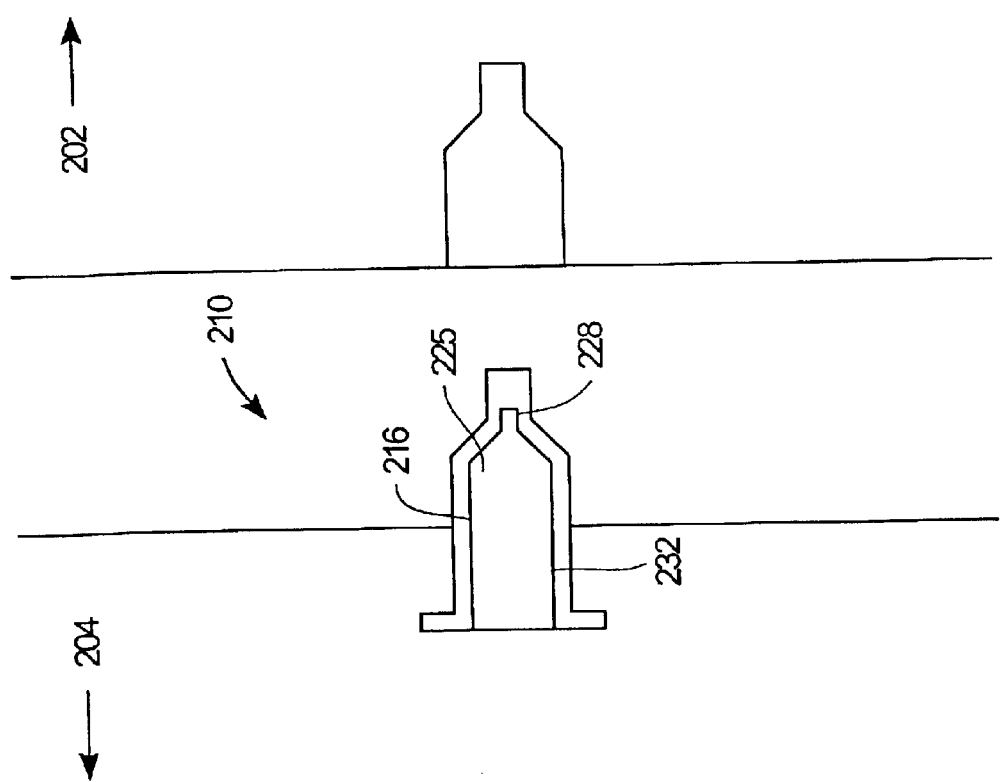
FIG. 21 shows the first half of the mold separated from the second half of the mold in accordance with an embodiment of the invention.
Figure 22:
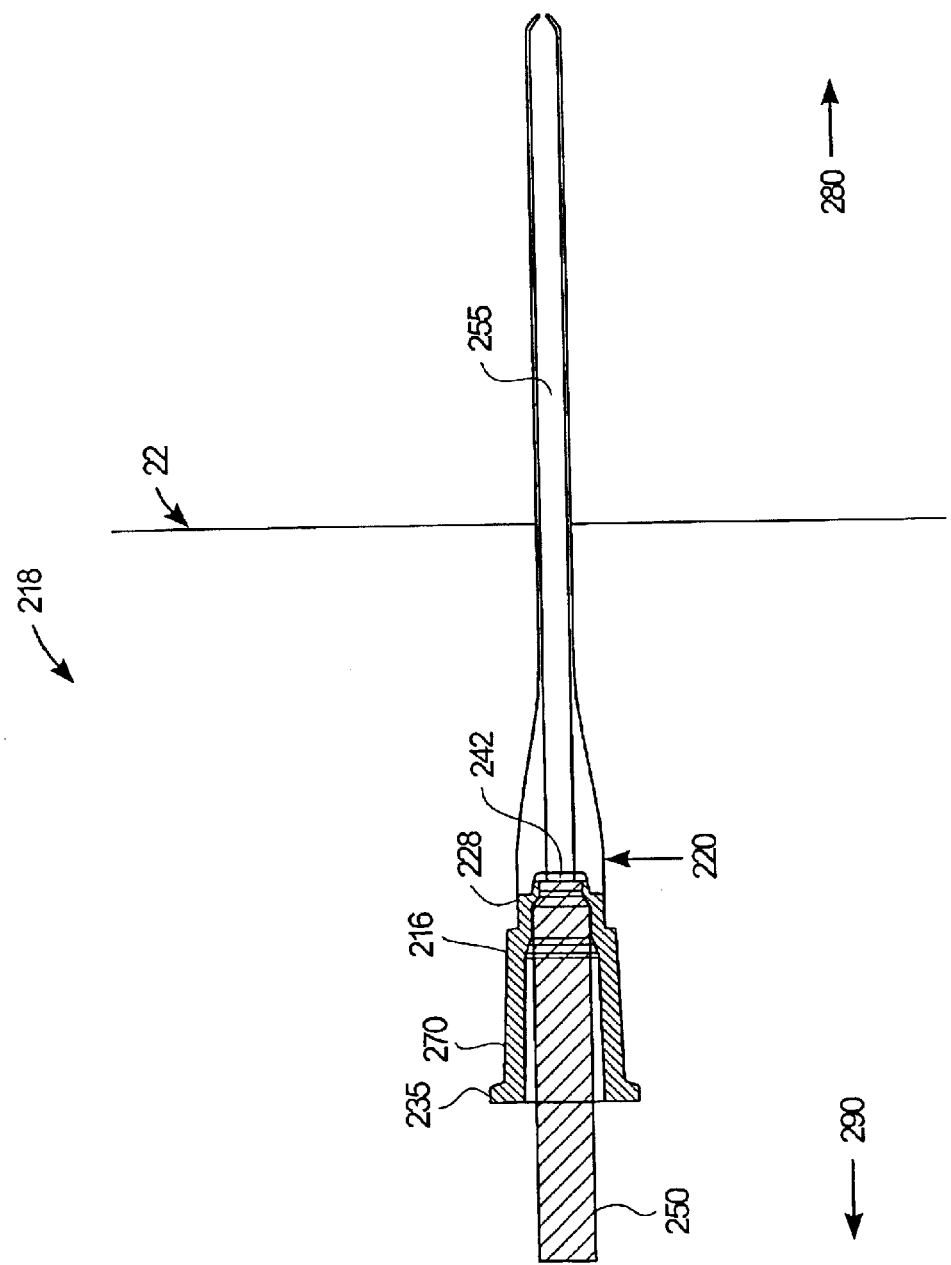
FIG. 22 shows the hub that was formed in FIGS. 18–20 is inserted into a second mold in accordance with an embodiment of the invention.
Figure 30:
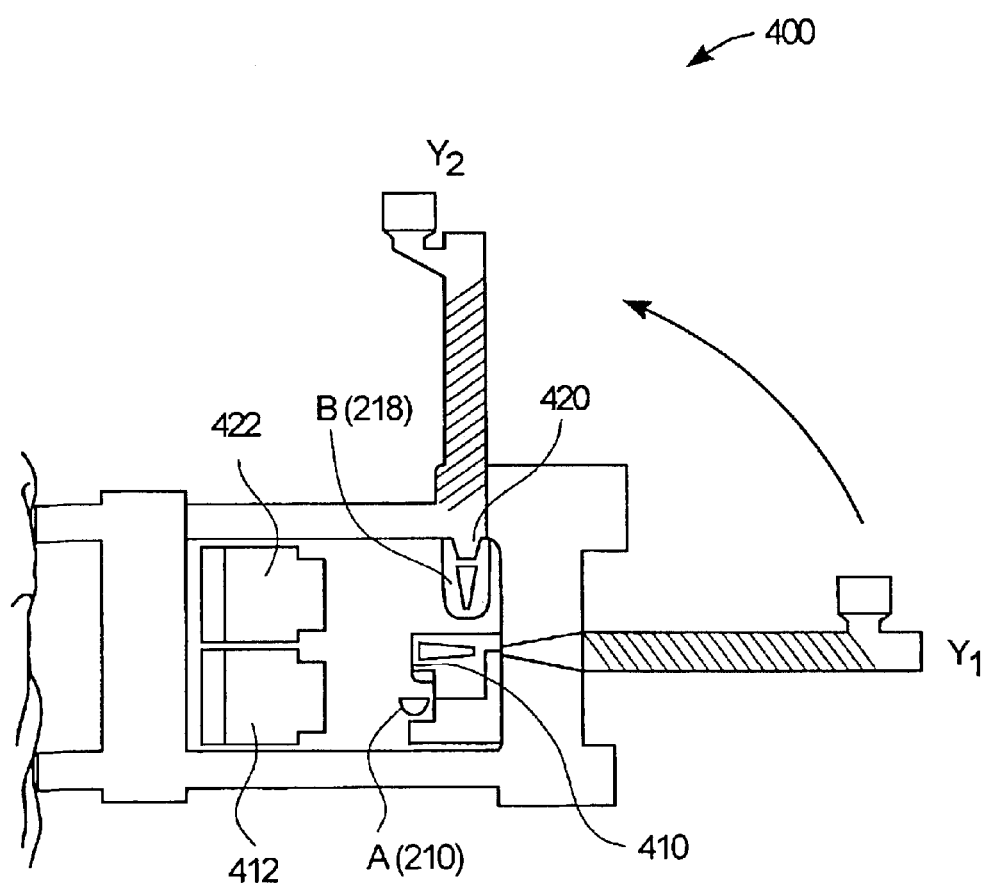
FIG. 30 shows an apparatus used to rotate the molds to different locations.

FIG. 21 shows in one embodiment that after the hub has been formed, first half 202 is separated from second half 204. The hub that is formed from first mold 210 is then ejected from second half 204 using traditional methods. It will be appreciated, however, that the hub may preferably remain in mold 210 and mold 210 is cycled or rotated around as shown in FIG. 30 and described in the accompanying text to second mold 218 wherein the hub is inserted into second mold 218. FIG. 22 shows the hub that was formed in the process disclosed in FIGS. 18–21 is thereafter inserted into a second mold 218. Second mold 218 has a tube cavity 255 for forming a tube at the distal end of the hub. FIG. 22 further shows first half 290 and second half 280 of second mold 218. First half 290 and second half 280 are mated together to ensure that the molten polymer stays within the cavity that is present within second mold 218. At the proximal portion of the hub, gas pin 250 is inserted thereto. Gas pin 250 is located within the inner diameter of hub. A fluid such as a gas (e.g., nitrogen gas, air, helium, argon, etc.) is injected at the proximal end of gas pin 250 and exits outlet 242 of gas pin 250. The molten polymer may be fed into a variety of locations for tube cavity 255. Inlet 220 shows one location that may be used for injecting molten polymer into tube cavity 255.

Figure 23:
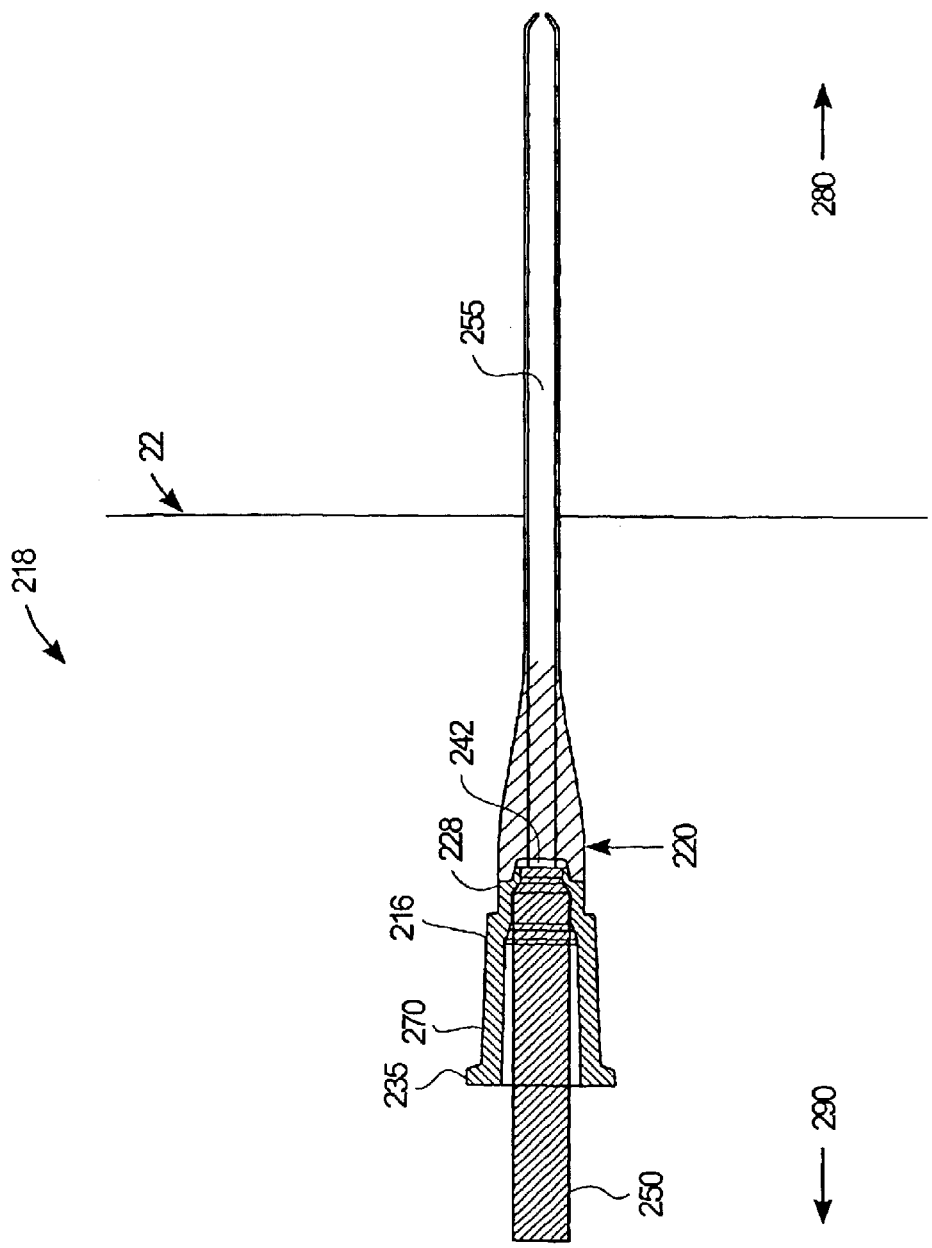
FIG. 23 shows a mold wherein molten polymer has been fed into a portion of the tube cavity in accordance with an embodiment of the invention.
Figure 24:
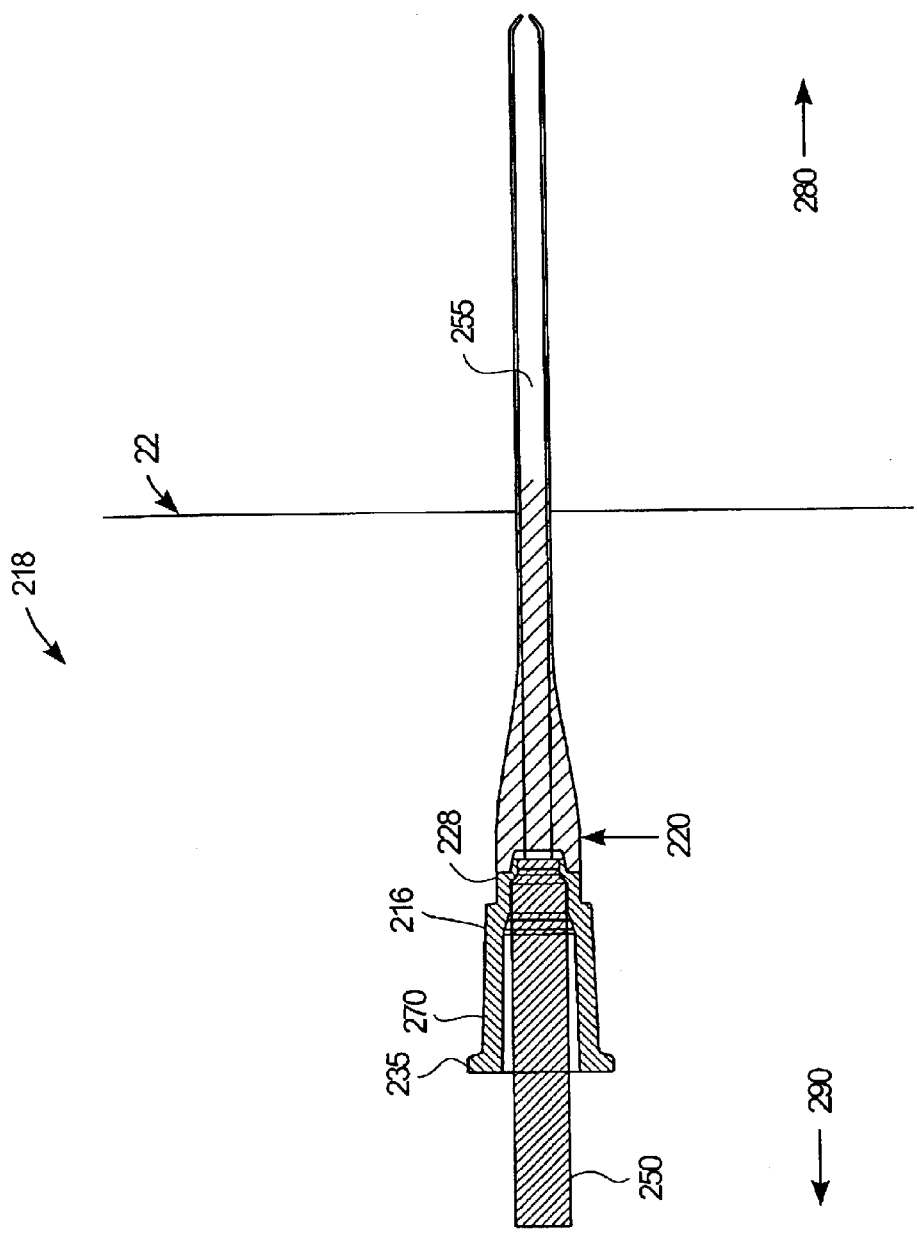
FIG. 24 shows the progression of the molten polymer moving from the proximal portion of the tube to the distal portion of the tube in accordance with an embodiment of the invention.

FIG. 23 shows second mold 218 wherein molten polymer has been fed into a portion of tube cavity 255. It should be noted that the type of polymer that may be used for the tube of the catheter may be different from the polymer that is fed into the hub or they may be the same polymer as explained above. Materials used to form the tube are described above. FIG. 24 shows the progression of the molten polymer moving from the proximal portion of the tube to the distal portion of the tube.

Figure 25:
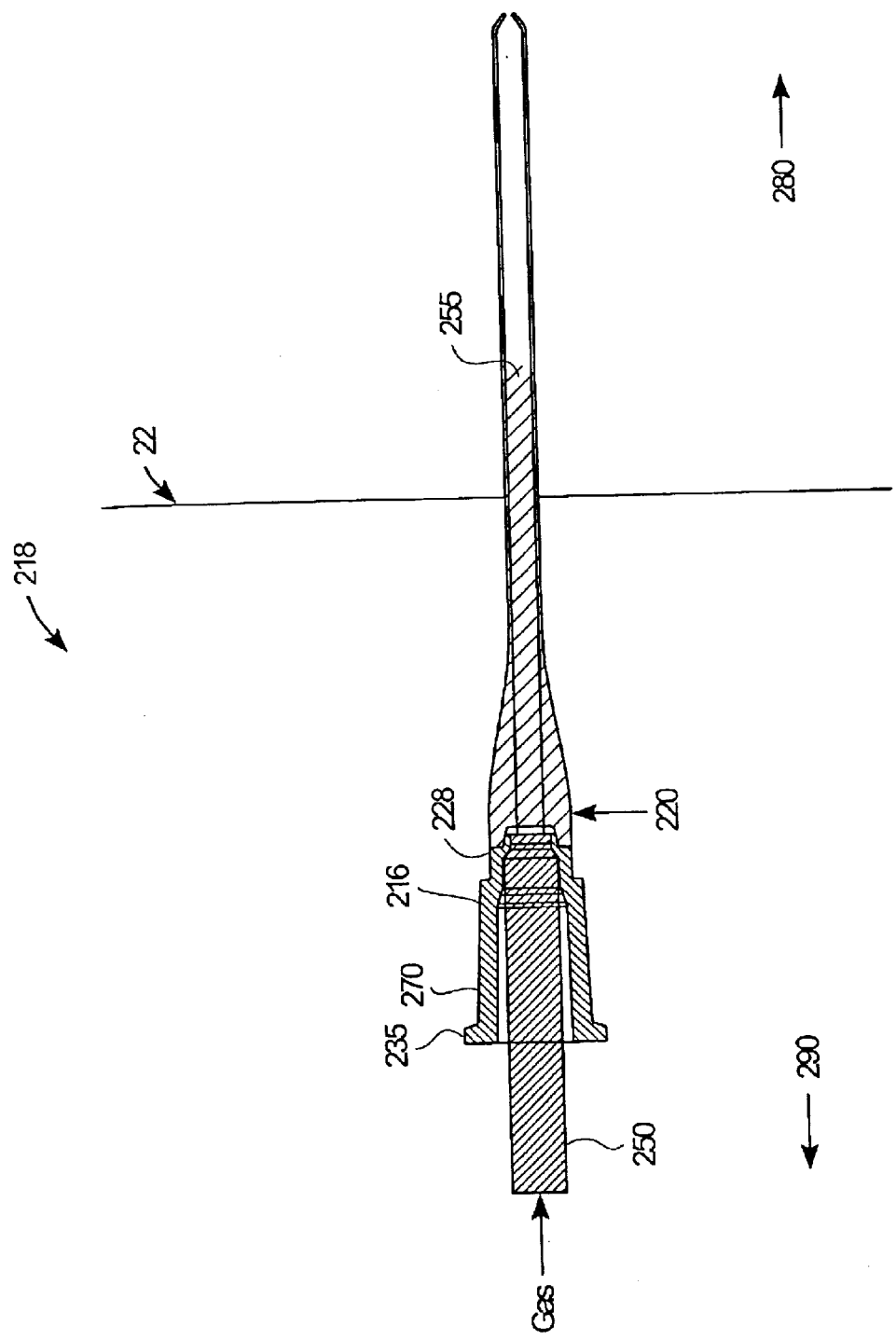
FIG. 25 shows the polymer continuing to move to the distal portion of the tube in accordance with an embodiment of the invention.
Figure 26:
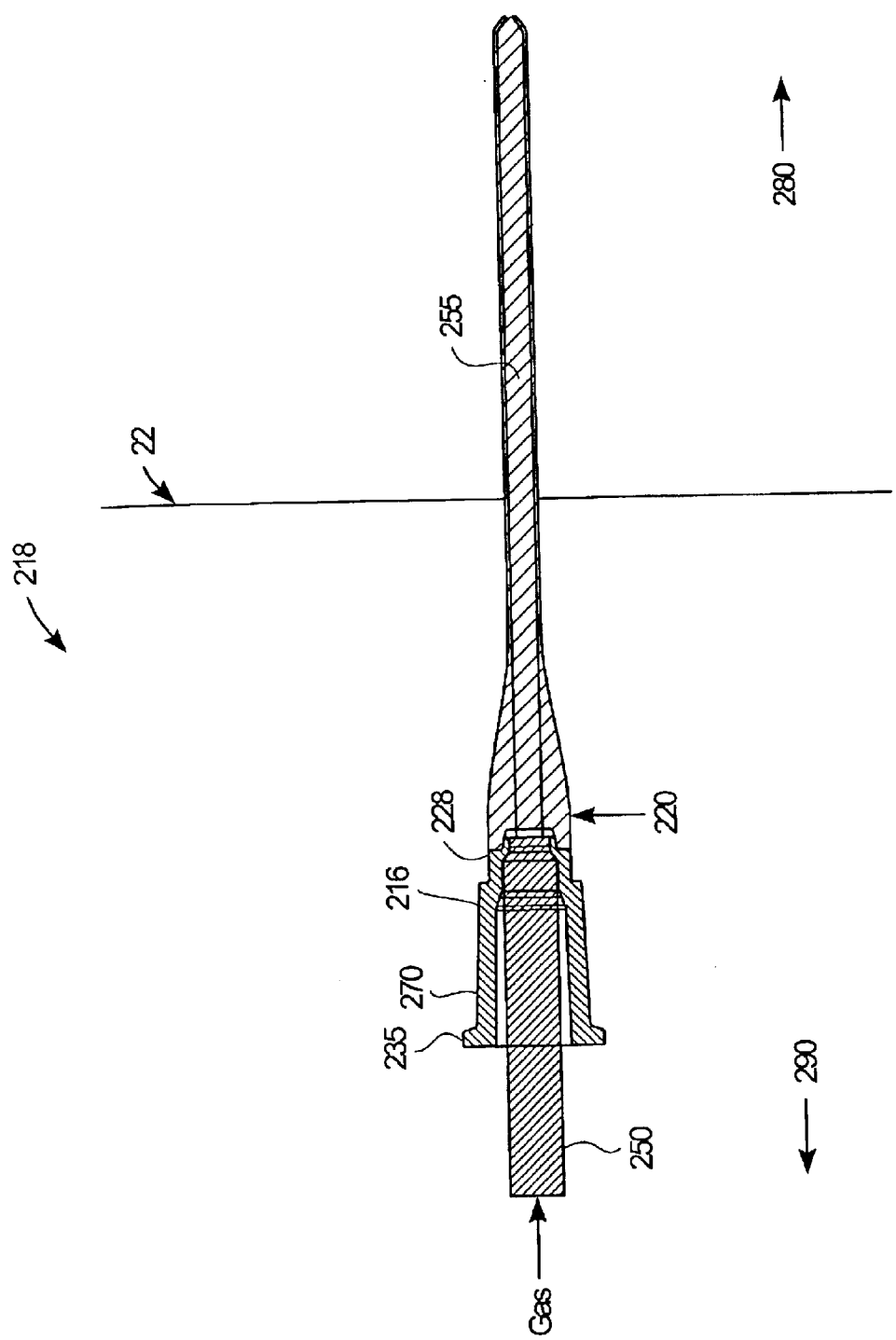
FIG. 26 continues to show the gas being injected into the gas pin and the polymer has almost filled the tube cavity in accordance with an embodiment of the invention.
Figure 27:
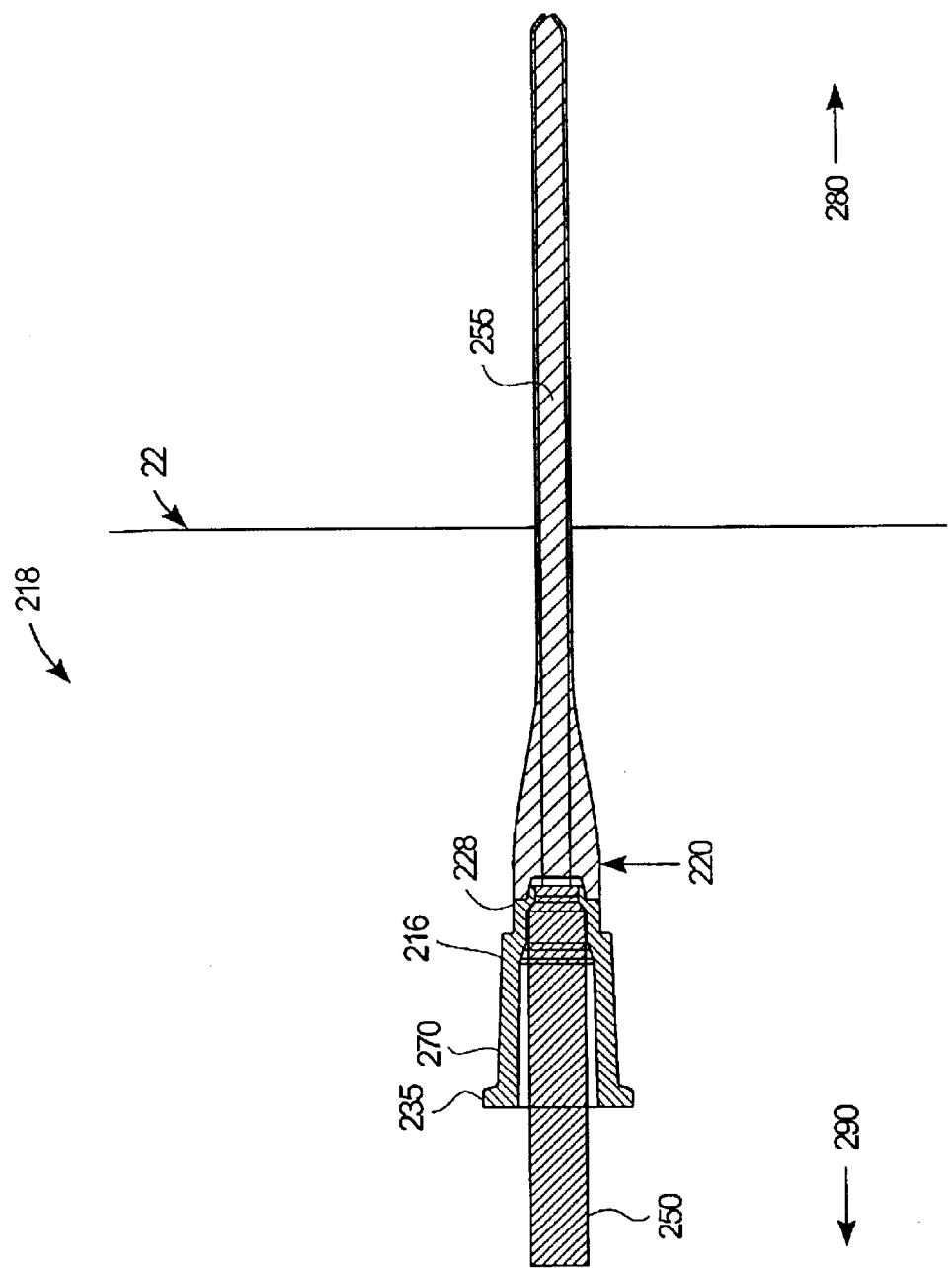
FIG. 27 shows that the gas injection has been terminated at the gas pin and the tube cavity is filled with polymer in accordance with an embodiment of the invention.

FIGS. 25–27 shows the polymer continuing to move to the distal portion of the tube cavity. Fluid such as gas is introduced at the proximal portion of gas pin 250 as shown in FIGS. 25 and 26. The pressure of the gas ranges from 500 psi to 9,000 psi and the gas is nitrogen gas, air, helium, argon, etc. The introduction of gas pushes the polymer to the distal portion of the tube leaving a polymer skin or tube wall next or adjacent to the mold surface and forming an internal lumen therein. As noted above, pressurized gas presses against the molten polymer causing the molten polymer to advance into regions of the cavity until the cavity is coated with molten polymer as shown in FIG. 27. A hollow channel is also formed inside of the tube cavity. It will be appreciated however, that the pressure of the gas may vary depending upon the material chosen. Other operating conditions may also vary depending upon the materials used to typically form the one-piece catheter. It generally takes up to 60 seconds (typically, it takes less than 15 seconds) from the time molten polymer is introduced until the first cavity is filled. FIG. 27 shows that the gas introduction has been terminated at gas pin 250 and the tube cavity 255 is filled with polymer with a hollow center therethrough.

Figure 28:
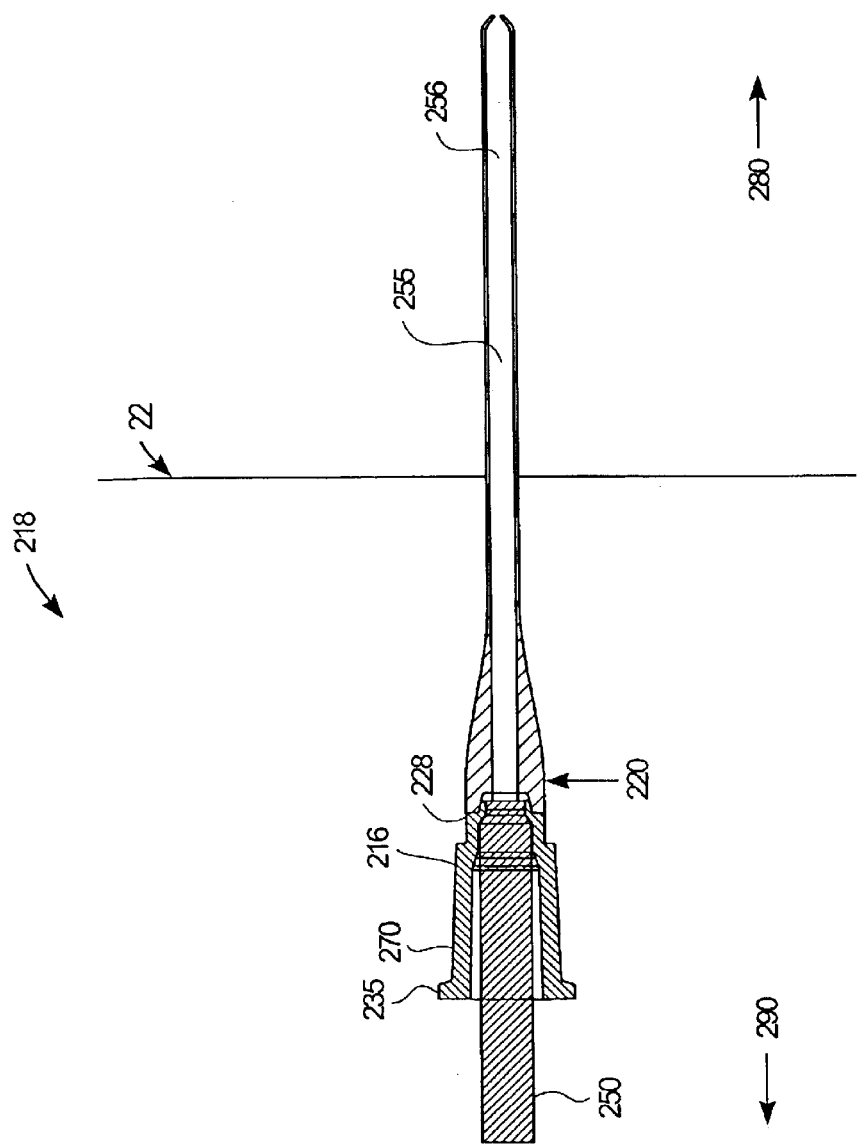
FIG. 28 shows a cross-section of the hollowed out portion of the tube formed for the intravascular device in accordance with an embodiment of the invention.

FIG. 28 further shows a cross-section of the tube being formed. It will be appreciated that the injection of the gas at gas pin 250 causes the tube to form a hollow central portion 256 of the tube as a result of gas assist injection molding manufacturing.

Figure 29:
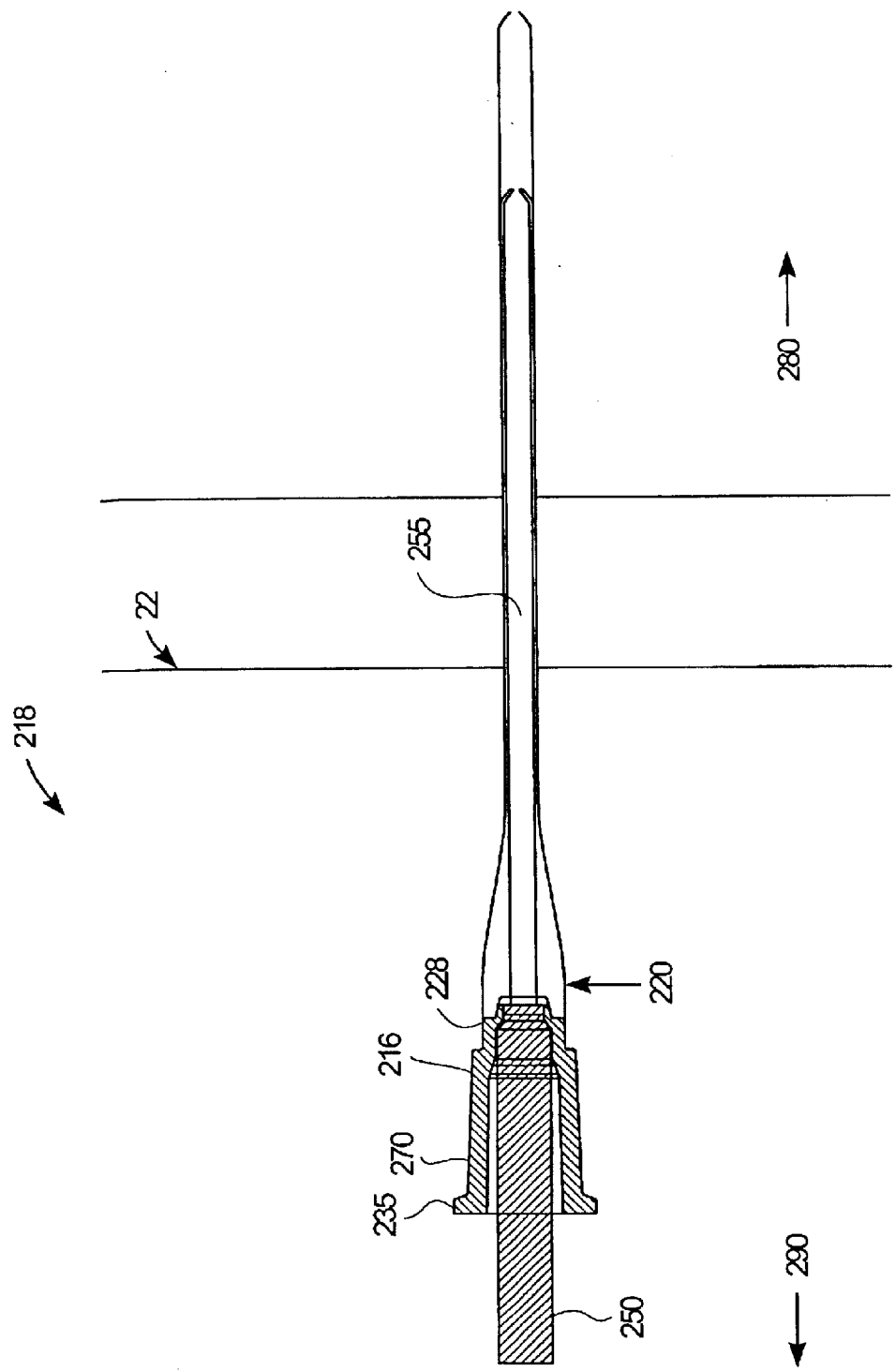
FIG. 29 shows the first half of the mold separated from the second half of the mold in accordance with an embodiment of the invention.

FIG. 29 shows first half 290 of mold 218 separated from second half 280 of second mold 218. The tube is formed and is partially separated from first half 280. The process represented by FIGS. 18–29 may then be repeated.

FIG. 30 illustrates a manufacturing apparatus 400 that may be used to move a first mold that is used to form a hub or a tube to a second mold to form the other portion of the one-piece catheter. In one embodiment, a rotating mechanism (not shown) is built into the mold itself.

There are two molds for forming a first and a second portion (A, B) of the one-piece catheter. The manufacturing operation begins by forming a first portion (A) in a first mold. The first mold is comprised of two sections (410, 412) that are mated together. After the first portion such as a hub has been formed, the first mold is disengaged from position Y1 and moved or rotated to position Y2. The second mold comprised of two sections (420, 422) that are mated together is then secured to the first mold using conventional techniques to allow the formation of a second portion using the second mold. It will be appreciated that instead of the second mold being secured to a first mold after the first portion is formed, the first portion may be released using conventional techniques and a robot (not shown) may pick up the first portion (A) and place it into the second mold. Thereafter, the second portion (B) may be formed using the molding process described herein. Other apparatus used for moving a first portion (A) after formation include devices that have a turntable for rotating the mold from one position to another. The process represented by FIGS. 18–30 may then be repeated.

FIGS. 31–36 show another embodiment of the invention. In this embodiment, the hub and the tube mold cavities are initially physically separated from one another by an insert located between the distal end of the hub and the proximal end of the tube.

Figure 31:
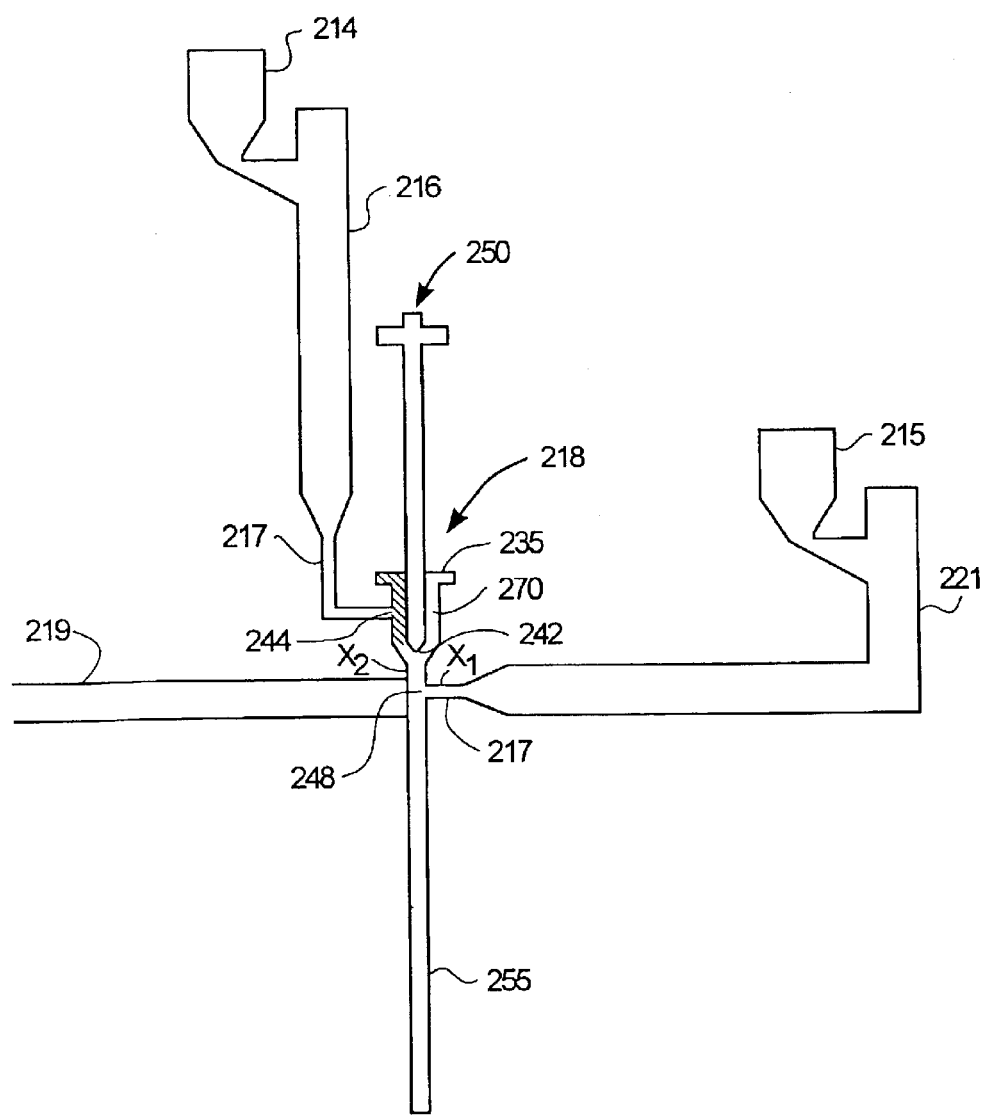
FIG. 31 shows the hub and tube cavity of the one-piece catheter and a portion of an apparatus used in multi-component injection molding in accordance with an embodiment of the invention.
Figure 32:
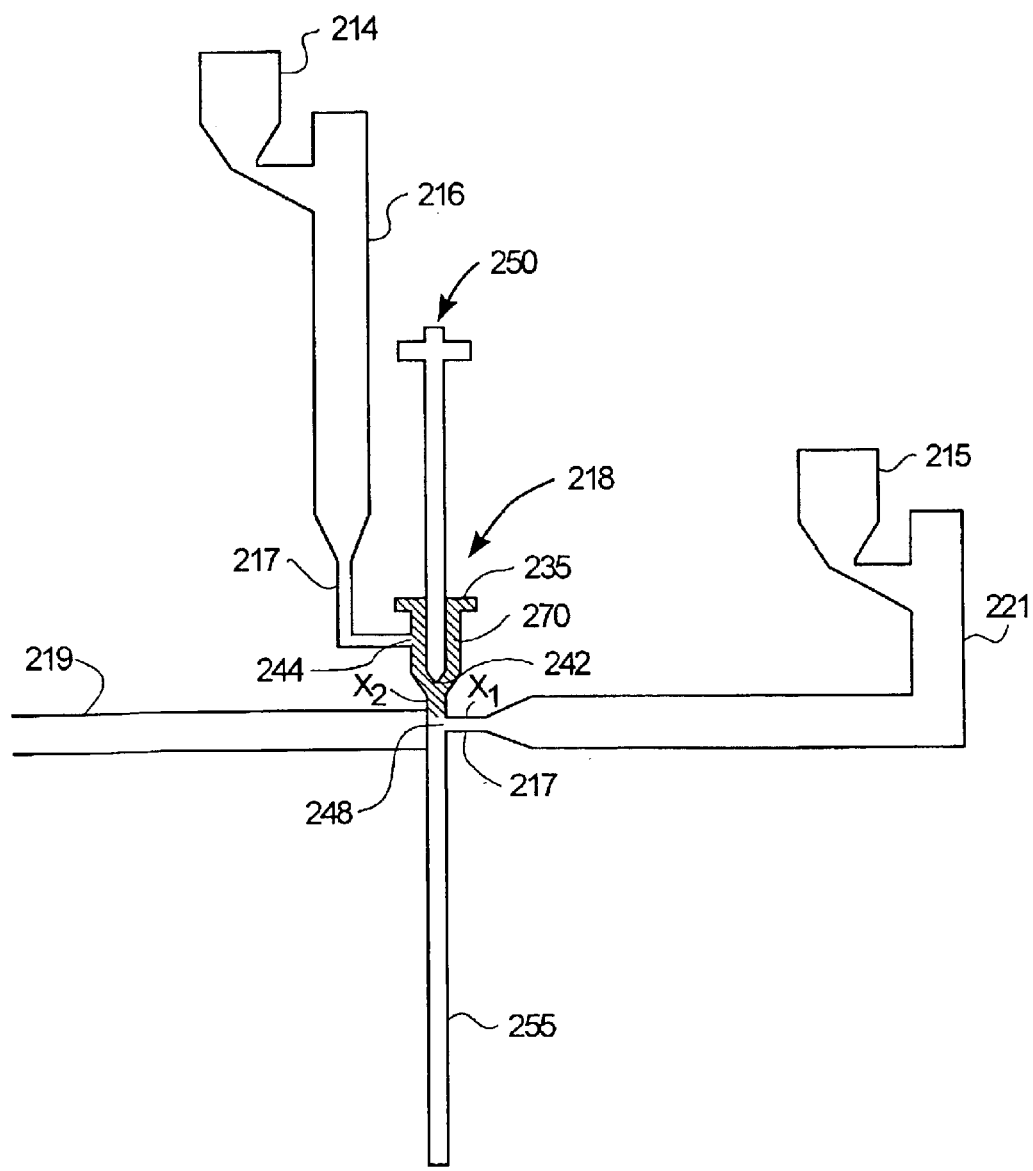
FIG. 32 shows molten polymer fed into a portion of the hub cavity in accordance with an embodiment of the invention.

FIG. 31 shows a portion of an apparatus for multi-component injection molding and the cavities used to form the hub and the tube. Containers 214 and 215 are hoppers used to hold solid polymer particles or granules. The first polymer is melted and enters first barrel 216 of a double barreled injection molding machine and exits from nozzle 217. The molten first polymer enters hub cavity 270 through a sprue(s) and runner(s) and into gate 244. Insert 219 at the distal end of hub cavity 270 may move from a first position ($X_1$) to a second position ($X_2$). In its first position, insert 219 blocks off hub cavity 270 from tube cavity 255. Gas pin 250 is inserted into the central portion of hub cavity 270 similar to that described above. FIG. 31 shows that a first polymer is injected into hub cavity 270 through gate 244 and molten polymer moves in two directions such as in the proximal direction of connector 235 and the distal direction of the hub nose. FIG. 32 shows the molten polymer has filled hub cavity 270. It will be appreciated that the central portion of the hub is hollow and only the outer structure of the hub is filled.

Figure 33:
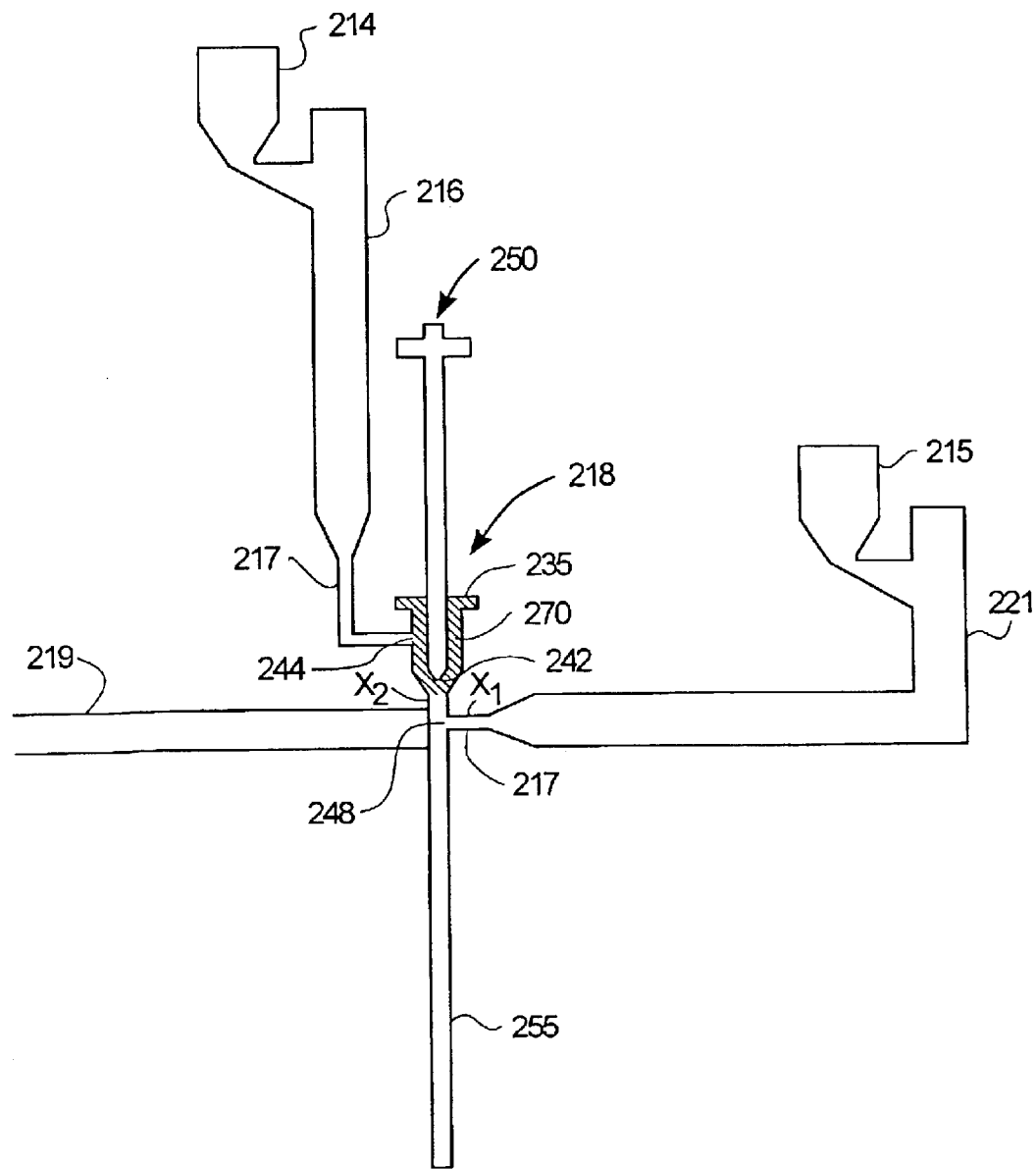
FIG. 33 shows an insert moving to a position allowing the first cavity and the second cavity to be in communication with one another in accordance with an embodiment of the invention.
Figure 34:
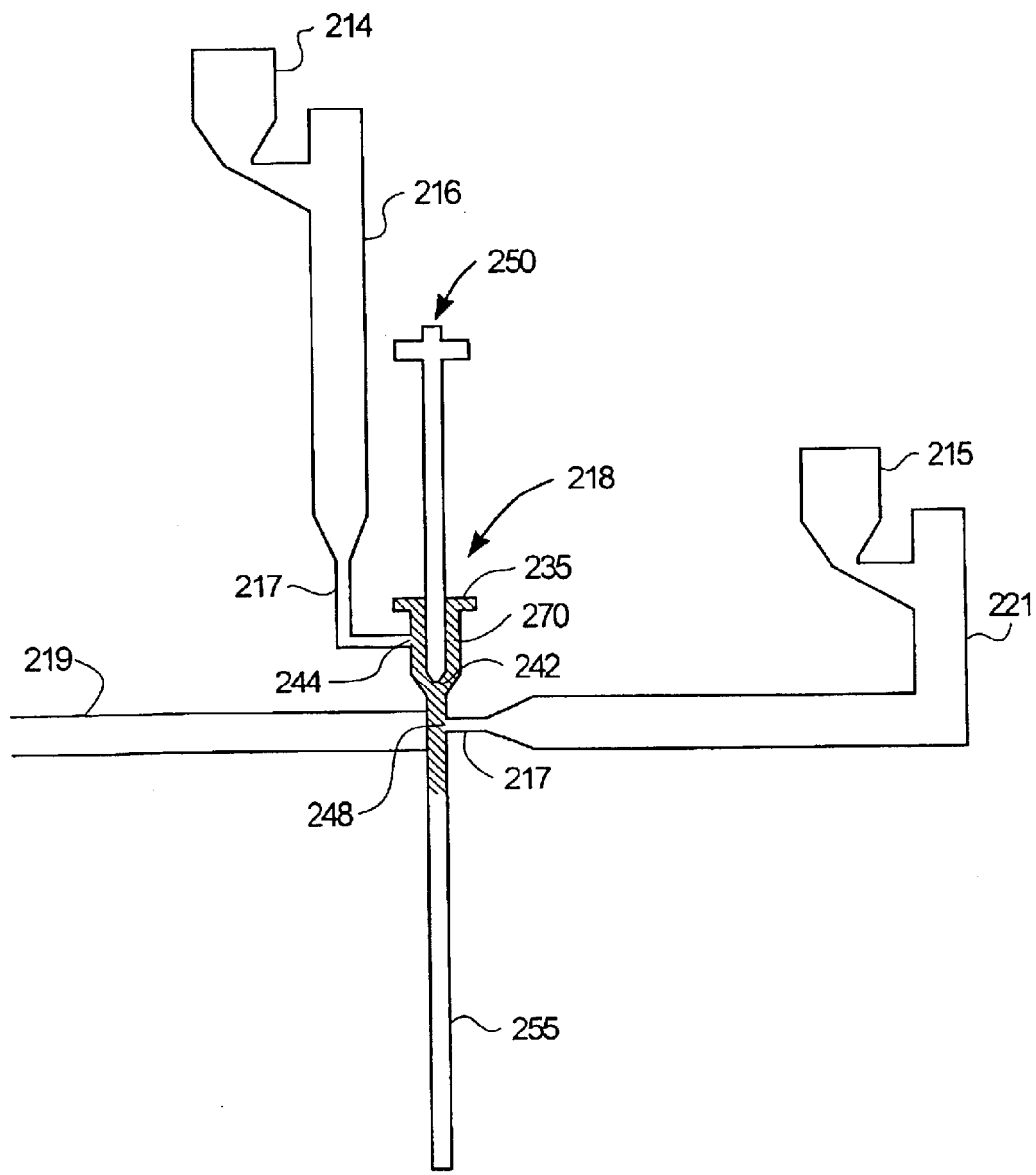
FIG. 34 shows a mold wherein the hub has been formed by a polymer and a portion of the tube is formed in accordance with an embodiment of the invention.
Figure 35:
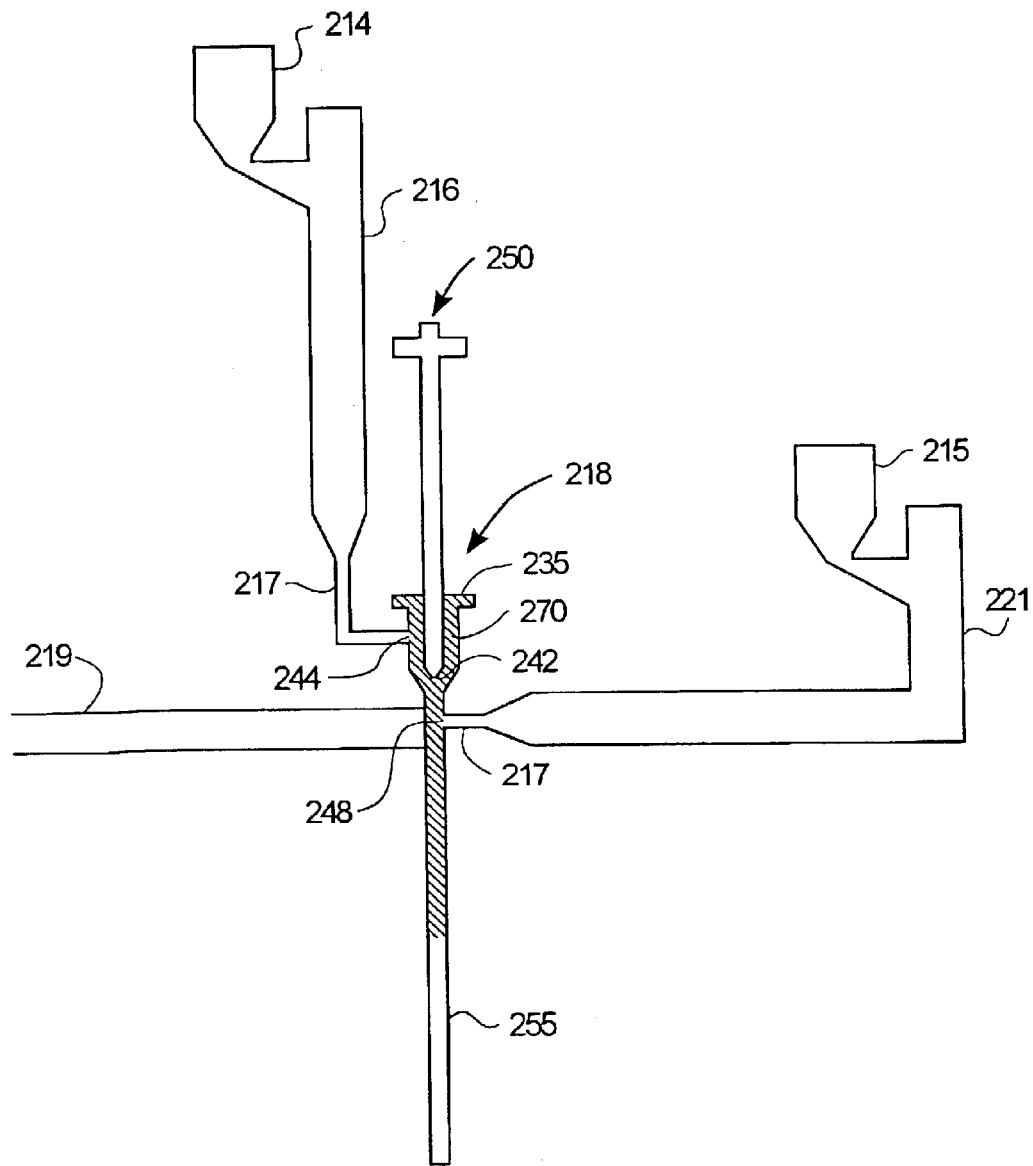
FIG. 35 shows polymer filling a portion of the tube cavity in accordance with an embodiment of the invention.

FIG. 33 shows insert 219 has moved to a second position $X_2$ from its prior position of $X_1$. This allows hub cavity 270 and tube cavity 255 to be in communication with one another and are no longer physically separated. At this point, the hub is formed and injection of a second polymer will combine at the interface with the first polymer. FIG. 34 shows that the second polymer has been fed into tube cavity 255 via hopper 215, barrel 221, and nozzle 223. The second polymer begins to move in the distal direction of tube cavity 255 through gate 248. In FIG. 35, a fluid such as a gas (e.g. air, nitrogen gas, helium, argon, etc.) is introduced at inlet 250. Gas exits gas pin at 242 wherein the gas pin is inserted through hub cavity 270 and ends at the distal end of the nose portion 240 of hub cavity 270. Gas pushes the central portion of the molten polymer to the distal portion of tube cavity 255 forming a tube.

Figure 36:
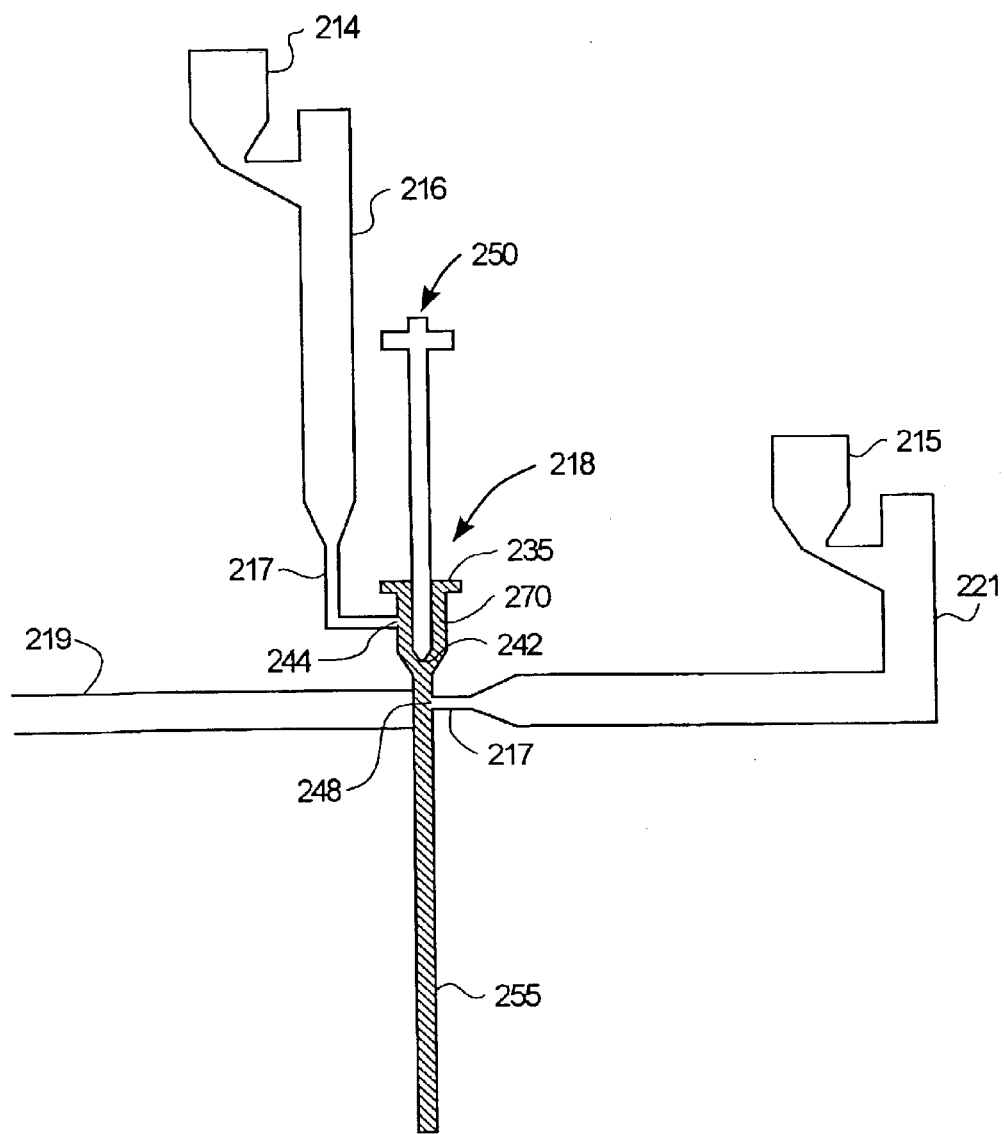
FIG. 36 shows the hub and tube have been formed in accordance with an embodiment of the invention.

FIG. 36 shows the tube cavity filled with polymer. However, it will be appreciated that the gas has cored out a longitudinal hollow portion through the tube that is formed. The hollow portion extends from the proximal end to the distal end of the tube.

The hub and tube are then ejected from the mold as a single piece using conventional methods. It will be appreciated that tube cavity 255 could be filled before hub cavity 270 but it is preferred that the hub cavity is filled prior to filling tube cavity 255. Alternatively, hub cavity 270 and tube cavity 255 may be filled with different polymers or the same polymer either simultaneously or at about the same time. The process represented by FIGS. 31–36 may then be repeated.

Figure 37:
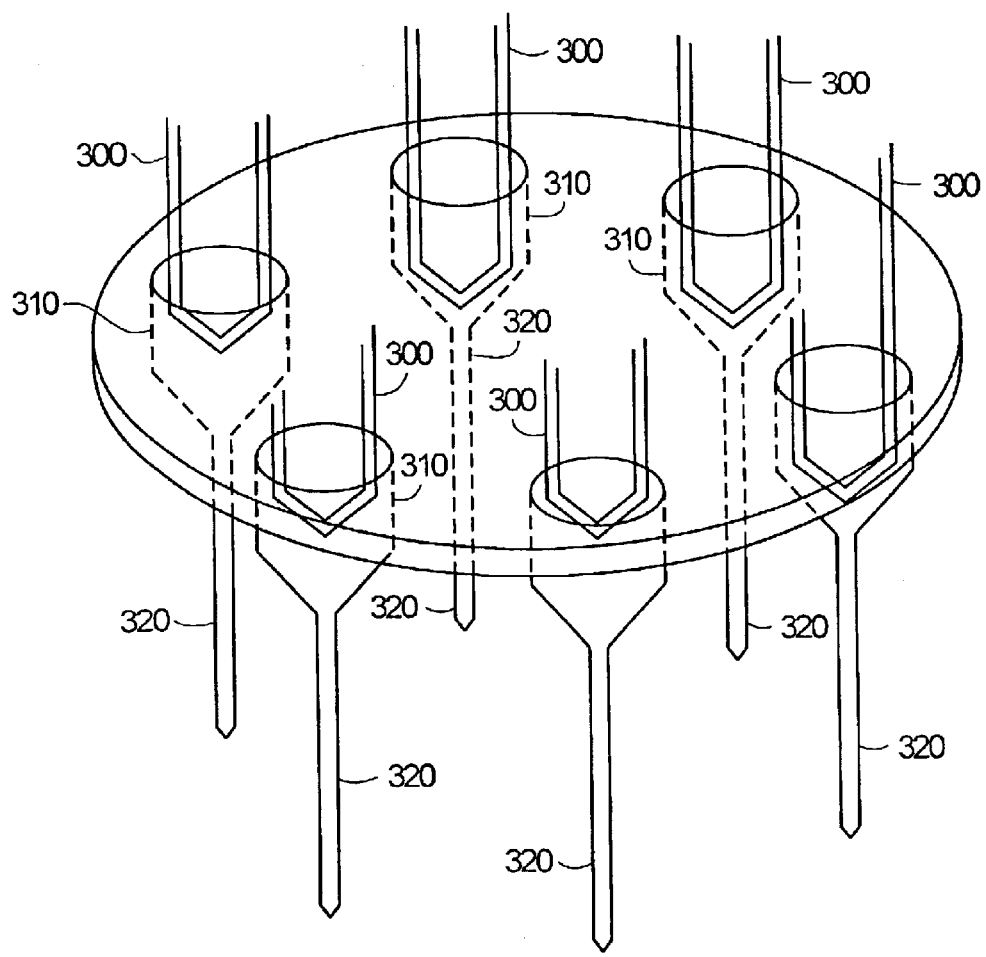
FIG. 37 shows a plurality of cavities in a mold used to form a hub and a tube.

FIG. 37 shows another mold wherein a plurality of cavities may be used to form an integral hub and a tube. Gas pin 300 is inserted into the hub portion 310 of the device. In this embodiment of the invention, a polymer is injected into the hub portion of the cavity. During or after the hub has been formed, the tube portion 320 of the intravascular device is formed. Either a single polymer may be used to form the hub and the tube or two polymers may be used separately to form the hub and the tube as a single piece.

FIG. 38 shows another mold that may be used to practice the invention. Runner 50 communicates with a plurality of tubes 16 and hubs 18. The polymer is heated in a molding machine (not shown) until the polymer attains a molten state. The polymer is introduced at 24 into the mold and generally moves in the direction of all the cavities simultaneously or about the same speed. Gas pin 20 is used to introduce a fluid such as a gas into the cavity of the mold. This mold may be used with a single polymer or two polymers.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. An apparatus for forming a single-piece catheter, comprising:
   a mold cavity with a tube portion having a beveled distal end and a hub portion extending from the tube portion, the mold cavity having a first orifice to receive a molt polymer and a second, separate orifice coupled to a gate to receive a gas which is injected under pressure into the gate.

2. The apparatus of claim 1, wherein the hub portion has a cavity for forming a lock at the proximal end of the hub portion, the lock is one of a male lock and a female lock.

3. The apparatus of claim 1, wherein the first and second orifices communicate through a common portion of the cavity.

4. The apparatus of claim 2, wherein the aspect ratio is greater than 200.

5. The apparatus of claim 2, wherein the lock is substantially cylindrical in shape.

6. The apparatus of claim 2, the orifice is located in the hub portion of the cavity.

7. The apparatus of claim 2, the orifice is located in the tube portion of the cavity.

8. An apparatus used for making a single-piece catheter, comprising:
   means for injecting a first polymer into a first cavity of a first mold to form a first portion;
   means for inserting the first portion into a second mold;
   means for injecting a second polymer into a second cavity of a second mold to form a second portion;
   means for injecting a fluid through an inlet of the second mold wherein the fluid pushes a second polymer forming a tube from a first length to a second length.

9. The apparatus of claim 8, wherein the second portion has a beveled distal end.

10. The apparatus of claim 8, wherein the first portion has a cavity for forming a lock at the proximal end of the first portion.

11. The apparatus of claim 8, wherein the lock is one of a male lock and a female lock.

12. The apparatus of claim 8, wherein the aspect ratio is greater than 200.

13. The apparatus of claim 8, wherein the lock is substantially cylindrical in shape.

14. The apparatus of claim 8, the orifice is located in the first portion of the cavity.

15. The apparatus of claim 8, the orifice is located in the tube portion of the cavity.

16. The apparatus of claim 8, wherein the first length of the second portion is hollow.

17. The apparatus of claim 8, wherein the second length of the second portion is hollow.

18. The apparatus of claim 8, wherein the first length of the second portion is solid.

19. The apparatus of claim 8, wherein the first portion is rotated from a first position to a second position; and the first portion is secured to a second mold.

20. A mold for forming a single-piece hub and tube comprising:
   a mold cavity with a tube portion and a hub portion extending from the tube portion, the mold cavity having a first orifice to receive a molten polymer and a second, separate orifice coupled to a gate to receive a gas which is injected under pressure into the gate;
   the hub portion has a connector portion at the proximal end of the hub portion;
   the tube portion has a distal end which is beveled; the mold being adapted for a first polymer to be injected into the hub portion; and a second polymer to be injected into the tube portion.

21. The apparatus of claim 20, wherein the connector portion is one of a male lock and a female lock.

22. The apparatus of claim 20 wherein the aspect ratio is greater than 200.

23. The apparatus of claim 20, wherein the connector portion is substantially cylindrical in shape.

24. The apparatus of claim 20, the orifice is located in at least one of the hub portion and tube portion of the cavity.

25. The apparatus of claim 20, wherein a hub portion which is formed is from the hub portion of the mold cavity is rotated by a rotator coupled to the mold from a first position to a second position; and the hub portion is secured to a second mold.

26. The apparatus of claim 20, wherein the first and second orifices communicate through a common portion of the cavity.

* * * * *

UNITED STATES PATENT AND TRADEMARK OFFICE
CERTIFICATE OF CORRECTION

PATENT NO. : 6,779,998 B2
DATED : August 24, 2004
INVENTOR(S) : David Goral et al.

It is certified that error appears in the above-identified patent and that said Letters Patent is hereby corrected as shown below:

Column 3,
Line 5, "shows the Theological properties" should read -- shows the rheological properties --

Column 5,
Line 48, "such as Theological properties" should read -- such as rheological properties --
Lines 55 and 60, "shows the Theological properties" should read -- shows the rheological properties --

Column 6,
Line 5, "(Theological properties not shown" should read -- (rheological properties not shown --

Column 13,
Line 62, "to receive a molt polymer" should read -- to receive a molten polymer --

Signed and Sealed this

Fifteenth Day of February, 2005

JON W. DUDAS
*Director of the United States Patent and Trademark Office*